United States Patent
Pikus et al.

(10) Patent No.: US 9,770,606 B2
(45) Date of Patent: Sep. 26, 2017

(54) ULTRASOUND ABLATION CATHETER WITH COOLING INFUSION AND CENTERING BASKET

(71) Applicant: Boston Scientific Scimed, Inc., Maple Grove, MN (US)

(72) Inventors: Michael J. Pikus, Golden Valley, MN (US); Kevin D. Edmunds, Ham Lake, MN (US); Mark L. Jenson, Greenfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 169 days.

(21) Appl. No.: 14/513,074

(22) Filed: Oct. 13, 2014

(65) Prior Publication Data

US 2015/0105715 A1   Apr. 16, 2015

Related U.S. Application Data

(60) Provisional application No. 61/891,241, filed on Oct. 15, 2013.

(51) Int. Cl.
  *A61N 7/02* (2006.01)
  *A61B 17/221* (2006.01)
  (Continued)

(52) U.S. Cl.
  CPC ...... *A61N 7/022* (2013.01); *A61B 2017/2212* (2013.01); *A61B 2018/00279* (2013.01);
  (Continued)

(58) Field of Classification Search
  CPC ............ A61N 7/022; A61N 2007/0043; A61B 2017/2212; A61B 2018/00797;
  (Continued)

(56) References Cited

U.S. PATENT DOCUMENTS

| 164,184 A | 6/1875 | Kidder |
| 852,787 A | 5/1907 | Hoerner |

(Continued)

FOREIGN PATENT DOCUMENTS

| DE | 10038737 A1 | 2/2002 |
| EP | 1053720 A1 | 11/2000 |

(Continued)

OTHER PUBLICATIONS

US 8,398,630, 03/2013, Demarais et al. (withdrawn)
(Continued)

*Primary Examiner* — Emily Schmidt
*Assistant Examiner* — Lauren M Peng

(57) ABSTRACT

Systems for nerve and tissue modulation are disclosed. An illustrative system may include an intravascular nerve modulation system including a catheter shaft, a first flexible mount, and a cylindrical ablation transducer. The ablation transducer may be affixed to the catheter shaft through the flexible mount to allow an infusion fluid to pass through a lumen of the transducer. Another illustrative system may include an intravascular nerve modulation system including an expandable basket for centering an ablation tra7nsducer within a lumen.

19 Claims, 8 Drawing Sheets

(51) Int. Cl.
 *A61B 18/00* (2006.01)
 *A61N 7/00* (2006.01)
(52) U.S. Cl.
 CPC .............. *A61B 2018/00404* (2013.01); *A61B 2018/00434* (2013.01); *A61B 2018/00511* (2013.01); *A61B 2018/00797* (2013.01); *A61B 2018/00875* (2013.01); *A61B 2218/002* (2013.01); *A61N 2007/0043* (2013.01)
(58) Field of Classification Search
 CPC  A61B 2018/00404; A61B 2018/00511; A61B 2218/002; A61B 2018/00875; A61B 2018/00279; A61B 2018/00434
 See application file for complete search history.

(56) References Cited

U.S. PATENT DOCUMENTS

| | | | |
|---|---|---|---|
| 921,973 A | 5/1909 | Gillett et al. |
| 976,733 A | 11/1910 | Gilliland |
| 1,167,014 A | 1/1916 | O'Brien |
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin |
| 3,952,747 A | 4/1976 | Kimmell |
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,531,943 A | 7/1985 | Van Tassel et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,890,623 A | 1/1990 | Cook et al. |
| 4,920,979 A | 5/1990 | Bullara et al. |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein et al. |
| 5,242,441 A | 9/1993 | Avitall |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,290,306 A | 3/1994 | Trotta et al. |
| 5,295,484 A | 3/1994 | Marcus |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Plueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock et al. |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,512,051 A | 4/1996 | Wang et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,161 A | 8/1996 | Imran |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory et al. |

(56) References Cited

U.S. PATENT DOCUMENTS

| | | |
|---|---|---|
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle et al. |
| 5,613,979 A | 3/1997 | Trotta et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg |
| 5,687,737 A | 11/1997 | Branham et al. |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,807,306 A | 9/1998 | Shapland et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford, III et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh et al. |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |

(56) References Cited

U.S. PATENT DOCUMENTS

| | | |
|---|---|---|
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,091,995 A | 7/2000 | Ingle et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,110,192 A | 8/2000 | Ravenscroft et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |

(56) References Cited

U.S. PATENT DOCUMENTS

| | | | |
|---|---|---|---|
| 6,442,413 | B1 | 8/2002 | Silver |
| 6,443,965 | B1 | 9/2002 | Gifford, III et al. |
| 6,445,939 | B1 | 9/2002 | Swanson et al. |
| 6,447,505 | B2 | 9/2002 | McGovern et al. |
| 6,447,509 | B1 | 9/2002 | Bonnet et al. |
| 6,451,034 | B1 | 9/2002 | Gifford, III et al. |
| 6,451,044 | B1 | 9/2002 | Naghavi et al. |
| 6,453,202 | B1 | 9/2002 | Knowlton |
| 6,454,737 | B1 | 9/2002 | Nita et al. |
| 6,454,757 | B1 | 9/2002 | Nita et al. |
| 6,454,775 | B1 | 9/2002 | Demarais et al. |
| 6,458,098 | B1 | 10/2002 | Kanesaka |
| 6,461,378 | B1 | 10/2002 | Knowlton |
| 6,468,276 | B1 | 10/2002 | McKay |
| 6,468,297 | B1 | 10/2002 | Williams et al. |
| 6,470,216 | B1 | 10/2002 | Knowlton |
| 6,470,219 | B1 | 10/2002 | Edwards et al. |
| 6,471,696 | B1 | 10/2002 | Berube et al. |
| 6,475,213 | B1 | 11/2002 | Whayne et al. |
| 6,475,215 | B1 | 11/2002 | Tanrisever |
| 6,475,238 | B1 | 11/2002 | Fedida et al. |
| 6,477,426 | B1 | 11/2002 | Fenn et al. |
| 6,480,745 | B2 | 11/2002 | Nelson et al. |
| 6,481,704 | B1 | 11/2002 | Koster et al. |
| 6,482,202 | B1 | 11/2002 | Goble et al. |
| 6,484,052 | B1 | 11/2002 | Visuri et al. |
| 6,485,489 | B2 | 11/2002 | Teirstein et al. |
| 6,488,679 | B1 | 12/2002 | Swanson et al. |
| 6,489,307 | B1 | 12/2002 | Phillips et al. |
| 6,491,705 | B2 | 12/2002 | Gifford, III et al. |
| 6,494,891 | B1 | 12/2002 | Cornish et al. |
| 6,497,711 | B1 | 12/2002 | Plaia et al. |
| 6,500,172 | B1 | 12/2002 | Panescu et al. |
| 6,500,174 | B1 | 12/2002 | Maguire et al. |
| 6,508,765 | B2 | 1/2003 | Suorsa et al. |
| 6,508,804 | B2 | 1/2003 | Sarge et al. |
| 6,508,815 | B1 | 1/2003 | Strul et al. |
| 6,511,478 | B1 | 1/2003 | Burnside et al. |
| 6,511,496 | B1 | 1/2003 | Huter et al. |
| 6,511,500 | B1 | 1/2003 | Rahme |
| 6,514,236 | B1 | 2/2003 | Stratienko |
| 6,514,245 | B1 | 2/2003 | Williams et al. |
| 6,514,248 | B1 | 2/2003 | Eggers et al. |
| 6,517,534 | B1 | 2/2003 | McGovern et al. |
| 6,517,572 | B2 | 2/2003 | Kugler et al. |
| 6,522,913 | B2 | 2/2003 | Swanson et al. |
| 6,522,926 | B1 | 2/2003 | Kieval et al. |
| 6,524,299 | B1 | 2/2003 | Tran et al. |
| 6,527,765 | B2 | 3/2003 | Kelman et al. |
| 6,527,769 | B2 | 3/2003 | Langberg et al. |
| 6,540,761 | B2 | 4/2003 | Houser |
| 6,542,781 | B1 | 4/2003 | Koblish et al. |
| 6,544,780 | B1 | 4/2003 | Wang |
| 6,546,272 | B1 | 4/2003 | MacKinnon et al. |
| 6,547,788 | B1 | 4/2003 | Maguire et al. |
| 6,549,800 | B1 | 4/2003 | Atalar et al. |
| 6,552,796 | B2 | 4/2003 | Magnin et al. |
| 6,554,780 | B1 | 4/2003 | Sampson et al. |
| 6,558,381 | B2 | 5/2003 | Ingle et al. |
| 6,558,382 | B2 | 5/2003 | Jahns et al. |
| 6,564,096 | B2 | 5/2003 | Mest |
| 6,565,582 | B2 | 5/2003 | Gifford, III et al. |
| 6,569,109 | B2 | 5/2003 | Sakurai et al. |
| 6,569,177 | B1 | 5/2003 | Dillard et al. |
| 6,570,659 | B2 | 5/2003 | Schmitt |
| 6,572,551 | B1 | 6/2003 | Smith et al. |
| 6,572,612 | B2 | 6/2003 | Stewart et al. |
| 6,577,902 | B1 | 6/2003 | Laufer et al. |
| 6,579,308 | B1 | 6/2003 | Jansen et al. |
| 6,579,311 | B1 | 6/2003 | Makower |
| 6,582,423 | B1 | 6/2003 | Thapliyal et al. |
| 6,589,238 | B2 | 7/2003 | Edwards et al. |
| 6,592,526 | B1 | 7/2003 | Lenker |
| 6,592,567 | B1 | 7/2003 | Levin et al. |
| 6,595,959 | B1 | 7/2003 | Stratienko |
| 6,600,956 | B2 | 7/2003 | Maschino et al. |
| 6,602,242 | B1 | 8/2003 | Fung et al. |
| 6,602,246 | B1 | 8/2003 | Joye et al. |
| 6,605,056 | B2 | 8/2003 | Eidenschink et al. |
| 6,605,084 | B2 | 8/2003 | Acker et al. |
| 6,623,452 | B2 | 9/2003 | Chien et al. |
| 6,623,453 | B1 | 9/2003 | Guibert et al. |
| 6,632,193 | B1 | 10/2003 | Davison et al. |
| 6,632,196 | B1 | 10/2003 | Houser |
| 6,645,223 | B2 | 11/2003 | Boyle et al. |
| 6,648,854 | B1 | 11/2003 | Patterson et al. |
| 6,648,878 | B2 | 11/2003 | Lafontaine |
| 6,648,879 | B2 | 11/2003 | Joye et al. |
| 6,651,672 | B2 | 11/2003 | Roth |
| 6,652,513 | B2 | 11/2003 | Panescu et al. |
| 6,652,515 | B1 | 11/2003 | Maguire et al. |
| 6,656,136 | B1 | 12/2003 | Weng et al. |
| 6,658,279 | B2 | 12/2003 | Swanson et al. |
| 6,659,981 | B2 | 12/2003 | Stewart et al. |
| 6,666,858 | B2 | 12/2003 | Lafontaine |
| 6,666,863 | B2 | 12/2003 | Wentzel et al. |
| 6,669,655 | B1 | 12/2003 | Acker et al. |
| 6,669,692 | B1 | 12/2003 | Nelson et al. |
| 6,673,040 | B1 | 1/2004 | Samson et al. |
| 6,673,064 | B1 | 1/2004 | Rentrop |
| 6,673,066 | B2 | 1/2004 | Werneth |
| 6,673,090 | B2 | 1/2004 | Root et al. |
| 6,673,101 | B1 | 1/2004 | Fitzgerald et al. |
| 6,673,290 | B1 | 1/2004 | Whayne et al. |
| 6,676,678 | B2 | 1/2004 | Gifford, III et al. |
| 6,679,268 | B2 | 1/2004 | Stevens et al. |
| 6,681,773 | B2 | 1/2004 | Murphy et al. |
| 6,682,541 | B1 | 1/2004 | Gifford, III et al. |
| 6,684,098 | B2 | 1/2004 | Oshio et al. |
| 6,685,732 | B2 | 2/2004 | Kramer |
| 6,685,733 | B1 | 2/2004 | Dae et al. |
| 6,689,086 | B1 | 2/2004 | Nita et al. |
| 6,689,148 | B2 | 2/2004 | Sawhney et al. |
| 6,690,181 | B1 | 2/2004 | Dowdeswell et al. |
| 6,692,490 | B1 | 2/2004 | Edwards |
| 6,695,830 | B2 | 2/2004 | Vigil et al. |
| 6,695,857 | B2 | 2/2004 | Gifford, III et al. |
| 6,699,241 | B2 | 3/2004 | Rappaport et al. |
| 6,699,257 | B2 | 3/2004 | Gifford, III et al. |
| 6,702,748 | B1 | 3/2004 | Nita et al. |
| 6,702,811 | B2 | 3/2004 | Stewart et al. |
| 6,706,010 | B1 | 3/2004 | Miki et al. |
| 6,706,011 | B1 | 3/2004 | Murphy-Chutorian et al. |
| 6,706,037 | B2 | 3/2004 | Zvuloni et al. |
| 6,709,431 | B2 | 3/2004 | Lafontaine |
| 6,711,429 | B1 | 3/2004 | Gilboa et al. |
| 6,712,815 | B2 | 3/2004 | Sampson et al. |
| 6,714,822 | B2 | 3/2004 | King et al. |
| 6,716,184 | B2 | 4/2004 | Vaezy et al. |
| 6,720,350 | B2 | 4/2004 | Kunz et al. |
| 6,723,043 | B2 | 4/2004 | Kleeman et al. |
| 6,723,064 | B2 | 4/2004 | Babaev |
| 6,736,811 | B2 | 5/2004 | Panescu et al. |
| 6,743,184 | B2 | 6/2004 | Sampson et al. |
| 6,746,401 | B2 | 6/2004 | Panescu |
| 6,746,464 | B1 | 6/2004 | Makower |
| 6,746,474 | B2 | 6/2004 | Saadat |
| 6,748,953 | B2 | 6/2004 | Sherry et al. |
| 6,749,607 | B2 | 6/2004 | Edwards et al. |
| 6,752,805 | B2 | 6/2004 | Maguire et al. |
| 6,760,616 | B2 | 7/2004 | Hoey et al. |
| 6,763,261 | B2 | 7/2004 | Casscells, III et al. |
| 6,764,501 | B2 | 7/2004 | Ganz |
| 6,769,433 | B2 | 8/2004 | Zikorus et al. |
| 6,770,070 | B1 | 8/2004 | Balbierz |
| 6,771,996 | B2 | 8/2004 | Bowe et al. |
| 6,773,433 | B2 | 8/2004 | Stewart et al. |
| 6,786,900 | B2 | 9/2004 | Joye et al. |
| 6,786,901 | B2 | 9/2004 | Joye et al. |
| 6,786,904 | B2 | 9/2004 | Döscher et al. |
| 6,788,977 | B2 | 9/2004 | Fenn et al. |
| 6,790,206 | B2 | 9/2004 | Panescu |
| 6,790,222 | B2 | 9/2004 | Kugler et al. |
| 6,796,981 | B2 | 9/2004 | Wham et al. |

(56) References Cited

U.S. PATENT DOCUMENTS

| | | |
|---|---|---|
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,923,808 B2 | 8/2005 | Taimisto |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |

(56) References Cited

U.S. PATENT DOCUMENTS

| | | | |
|---|---|---|---|
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,480 B2 | 1/2008 | Eidenschink et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,686,841 B2 | 3/2010 | Eidenschink et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |

(56) References Cited

U.S. PATENT DOCUMENTS

| | | |
|---|---|---|
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,043,673 B2 | 10/2011 | Lee et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,168,275 B2 | 5/2012 | Lee et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |

(56) References Cited

U.S. PATENT DOCUMENTS

| | | |
|---|---|---|
| 8,488,591 B2 | 7/2013 | Miali et al. |
| 2001/0007070 A1 | 7/2001 | Stewart et al. |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0050635 A1 | 3/2003 | Truckai et al. |
| 2003/0065317 A1 | 4/2003 | Rudie et al. |
| 2003/0092995 A1 | 5/2003 | Thompson |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2003/0229340 A1 | 12/2003 | Sherry et al. |
| 2003/0233099 A1 | 12/2003 | Danaek et al. |
| 2004/0010118 A1 | 1/2004 | Zerhusen et al. |
| 2004/0019348 A1 | 1/2004 | Stevens et al. |
| 2004/0019349 A1* | 1/2004 | Fuimaono ......... A61B 17/22012 606/41 |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0080374 A1 | 4/2005 | Esch et al. |
| 2005/0096647 A1 | 5/2005 | Steinke et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2005/0273149 A1 | 12/2005 | Tran et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0085054 A1 | 4/2006 | Zikorus et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0182873 A1 | 8/2006 | Klisch et al. |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0067883 A1 | 3/2007 | Sretavan |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0179496 A1 | 8/2007 | Swoyer et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |

(56) References Cited

U.S. PATENT DOCUMENTS

| | | |
|---|---|---|
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0256623 A1* | 10/2010 | Nicolas .............. A61B 18/04 606/27 |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |

(56) References Cited

U.S. PATENT DOCUMENTS

| | | |
|---|---|---|
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1* | 6/2012 | Jenson ............... A61B 18/1492 606/41 |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramanaim et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |
| 2014/0074083 A1 | 3/2014 | Horn et al. |
| 2014/0163372 A1* | 6/2014 | Deladi ............... A61B 18/04 600/439 |

FOREIGN PATENT DOCUMENTS

| | | |
|---|---|---|
| EP | 1180004 A1 | 2/2002 |
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |

(56) References Cited

FOREIGN PATENT DOCUMENTS

| | | |
|---|---|---|
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 9935986 | 7/1999 |
| WO | 0047118 A1 | 8/2000 |
| WO | 0066021 | 11/2000 |
| WO | 0195820 | 12/2001 |
| WO | 03026525 A1 | 4/2003 |
| WO | 2004100813 A2 | 11/2004 |
| WO | 2004110258 A2 | 12/2004 |
| WO | 2005041810 | 5/2005 |
| WO | 2006105121 A2 | 10/2006 |
| WO | 2008014465 A2 | 1/2008 |
| WO | 2009121017 A1 | 10/2009 |
| WO | 2010067360 A2 | 6/2010 |
| WO | 2010102310 A2 | 9/2010 |
| WO | 2010132703 | 11/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | 2011130534 A2 | 10/2011 |
| WO | 2012019156 A1 | 2/2012 |
| WO | 2013049601 A2 | 4/2013 |

OTHER PUBLICATIONS

CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50(2): 218-223, Feb. 2003.
Lazebnik et al., "Tissue Strain Analytics Virtual Touch Tissue Imaging and Qualification," Siemens Whitepaper, 7 pages, Oct. 2008.
Han et al., "Third-Generation Cryosurgery for Primary and Recurrent Prostate Caner," BJU International, vol. 93: 14-18, 2004.
Zhou et al., "Mechanism Research of Cryoanalgesia," Neurological Research, Forefront Publishing Group, 17: 307-311, Aug. 1995.
Florete, "Cryoblative Procedure for Back Pain," Jacksonville Medicine, Oct. 1998, 10 pages, printed Dec. 2009.
Stevenson, "Irrigated RF Ablation: Power Titration and Fluid Management for Optimal Safety Efficacy," 4 pages, 2005.
Giliatt et al., "The Cause of Nerve Damage in Acute Compression," Trans Am Neurol Assoc, 99: 71-4, 1974.
Omura et al., "A Mild Acute Compression Induces Neurapraxia in Rat Sciatic Nerve," The International Journal of Neuroscience, vol. 114 (12):1561-1572, Dec. 2004.
Baun, "Interaction with Soft Tissue," Principles of General & Vascular Sonography, Chapter 2, pp. 23-24, Before Mar. 2012.
Blue Cross Blue Shield Medical Policy, "Surgery Section—MRI-Guided Focused Ultrasound (MRgFUS) for the Treatment of Uterine Fibroids and Other Tumors," 5 pages, printed Oct. 19, 2009.
Gentry et al., "Combines 3D Intracardiac Echo and Ultrasound Ablation," Medical Imaging 2003: Ultrasonic and Signal Processing, 5035: 166-173, 2003.
Lafon et al., "Optmizing the Shape of Ultrasound Transducers for Interstitial Thermal Ablations," MEd Phys. Mar. 2002; 29(3): 290-7 (abstract only), Mar. 2002.
G. Ter Haar, "Ultrasound Focal Beam Surgery," Ultrasound in Med. & Biol., 1995, 21(9): 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, 7562: 1-10, 2010.
Zhou et al., "Non-Thermal Ablation of Rabbit Liver VX2 Tumore by Pulsed High Intensity Focused Ultrasound Contrast Agent: Pathological Characteristics," World Journal of Gastroenterology, 14(43): 6743-6747, Nov. 21, 2008.
Van Den Berg, "Light echoes image the human body," OLE, p. 35-37, Oct. 2001.
"IntraLuminal: Products," IntraLuminal Therapeutics, Inc., p. 1-9, 2003.
"Laser Catheter to Aid Coronary Surgery," TechTalk: MIT, p. 1-4, Jan. 9, 1991.
"Optical Coherence Tomography: LightLab Imaging Starts US Cardiology Clinical Investigations," LightLab Imaging Technology Company Press Release, Jun. 25, 2002, <http://www.lightlabimaging.com/press/cardtrails.html> 2 pages.
"Optical Coherence Tomography: LightLab Sees Bright Prospects for Cardiac Application of OCT Technology," LightLab Imaging Technology, The Gray Sheet, Medical Devices, Diagnostics, & Instrumentation, 27(35), Aug. 27, 2001, <http://www.lightlabimaging.com/press/graysheet.html> 1 page.
"Products—Functional Measurement," Volcano Functional Measurement Products US, p. 1-2, Mar. 24, 2003.
Brown et al., "Radiofrequency capacitive heaters: the effect of coupling medium resistivity on power absorption along a mouse leg," Physics in Medicine and Biology, 38: 1-12, 1993.
Carrington, "Future of CVI: It's all about plaque: Identification of vulnerable lesions, not 'rusty pipes,' could become cornerstone of preventive cardiology," Diagnostic Imaging Special Edition Forum, 5 pages total, retrieved on Sep. 3, 2003.
Chen et al., "Percutaneous pulmonary artery denervation completely abolishes experimental pulmonary arterial hypertension in vivo," EuroIntervention, p. 1-8, 2013.
Cimino, "Preventing plaque attack," Mass High Tech, 3 pages total, retrieved on Sep. 3, 2003 <http://Masshightech.com/displayarticledetail.ap?art_id=52283&cat_id=10>, 2001.
Dahm et al., "Relation of Degree of Laser Debulking of In-Stent Restenosis as a Predictor of Restenosis Rate," The American Journal of Cardiology, 90:68-70, 2002.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," 7 pages, Fourth Edition, Oct. 1986.
Pieper et al. "Design and implementation of a new computerized system for intraoperative cardiac mapping", J. Appl. Physiol. 71(4): 1529-1539, 1991.
Fournier-Desseux et al., "Assessment of 1-lead and 2-lead electrode patterns in electrical impedance endotomography," Physiological Measurement, Institute of Physics Publishing, 26:337-349, 2005.
Fram et al., "Feasibility of Radiofrequency Powered, Thermal Balloon Ablation of Atrioventricular Bypass Tracts Via the Coronary Sinus: In Vivo Canine Studies," Pace, 18:1518-1530, Aug. 1995.
Fram et al., "Low Pressure Radiofrequency Balloon Angioplasty: Evaluation in Porcine Peripheral Arteries," JACC, American College of Cardiology, 21(6):1512-1521, 1993.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," p. 1-21, 1999.
Gabriel, "Appendix C: Modeling the frequency dependence of the dielectric properties to a 4 dispersions spectrum," p. 1-49, Nov. 6, 1997.
Gregory et al., "Liquid Core Light Guide for Laser Angioplasty," The Journal of Quantum Electronics, 26 (12):2289-2296, Dec. 1990.

(56) References Cited

OTHER PUBLICATIONS

Kaplan et al., "Healing after Arterial Dilatation with Radiofrequency Thermal and Nonthermal Balloon Angioplasty Sytems," Journal of Investigative Surgery, 6:33-52, 1993.

Kolata, "New Studies Question Value of Opening Arteries," The New York Times [online], 5 pages total, <http://nytimes.com/2004/03/21/health/21HEAR.html?ei=5070&en=641bc03214e&ex=11067>, Mar. 21, 2004.

Konings et al., "Development of an Intravascular Impedance Catheter for Detection of Fatty Lesions in Arteries," IEEE Transactions on Medical Imaging, 16(4):439-444, Aug. 1997.

Kurtz et al., "Lamellar Refractive Surgery with Scanned Intrastromal Picosecond and Femtosecond Laser Pulses in Animal Eyes," Journal of Refractive Surgery, 14:541-548, Sep./Oct. 1998.

Lee et al., "Thermal Compression and Molding of Atherosclerotic Vascular Tissue With Use of Radiofrequency Energy: Implications for Radiofrequency Balloon Angioplasty," JACC, American College of Cardiology, 13(5):1167-1175, 1989.

Lima et al., "Efficacy and Safety of Oral Sirolimus to Treat and Prevent In-Stent Restenosis: A Pilot Study Results," American Heart Association, p. 2929, 2002.

Lima et al., "Systemic Immunosuppression Inhibits In-Stent Coronary Intimal Proliferation in Renal Transplant Patients," American Heart Association, p. 2928, 2002.

Morice et al., "A Randomized Comparison of a Sirolimus-Eluting Stent With a Standard Stent for Coronary Revascularization," The New England Journal of Medicine, 346(23):1773-1780, Jun. 6, 2002.

Muller-Leisse et al., "Effectiveness and Safety of Ultrasonic Atherosclerotic Plaque Ablation: In Vitro Investigation," CardioVascular and Interventional Radiology, 16:303-307, 1993.

Nair et al., "Regularized Autoregressive Analysis of Intravascular Ultrasound Backscatter: Improvement in Spatial Accuracy of Tissue Maps," IEEE Transactions on Ultrasonics, 51(4):420-431, Apr. 2004.

Popma et al., "Percutaneous Coronary and Valvular Intervention," Braunwald's Heart Disease: A Textbook of Cardiovascular Medicine, 7th edition, p. 1364-1405, 2005.

Resar et al., "Endoluminal Sealing of Vascular Wall Disruptions With Radiofrequency-Heated Balloon Angioplasty," Catheterization and Cardiovascular Diagnosis, 29:161-167, 1993.

Romer et al., "Histopathology of Human Coronary Atherosclerosis by Quantifying Its Chemical Composition With Raman Spectroscopy," Circulation, 97:878-885, 1998.

Schauerte et al., "Catheter Ablation of Cardiac Autonomic Nerves for Prevention of Vagal Atrial Fibrillation," Circulation, 102:2774-2780, 2000.

Scheller et al., "Intracoronary Paclitaxel Added to Contrast Media Inhibits In-Stent Restenosis of Porcine Coronary Arteries," American Heart Association, p. 2227, 2002.

Scheller et al., "Potential solutions to the current problem: coated balloon," EuroIntervention, 4(Supplement C): C63-C66, 2008.

Shaffer, "Scientific basis of laser energy," Clinics in Sports Medicine, 21:585-598, 2002.

Shmatukha et al., "MRI temperature mapping during thermal balloon angioplasty," Physics in Medicine and Biology, 51:N163-N171, 2006.

Slager et al., "Vaporization of Atherosclerotic Plaques by Spark Erosion," J Am Coll Cardiol, p. 21-25, 1985.

Stiles et al., "Simulated Characterization of Atherosclerotic Lesions in the Coronary Arteries by Measurement of Bioimpedance," IEEE Transactions on Biomedical Engineering, 50(7): 916-921, Jul. 2003.

Suselbeck et al., "In vivo intravascular electric impedance spectroscopy using a new catheter with integrated microelectrodes," Basic Res Cardiol, 100:28-34, 2005.

Suselbeck et al., "Intravascular electric impedance spectroscopy of atherosclerotic lesions using a new impedance catheter system," Basic Res Cardiol, 100:446-452, 2005.

Tepe et al., "Local Delivery of Paclitaxel to Inhibit Restenosis during Angioplasty of the Leg," The New England Journal of Medicine, 358:689-699, 2008.

"Optical Coherence Tomography: Advantages of OCT," LightLab Imaging Technology, printed Sep. 3, 2003.

"Optical Coherence Tomography: Image Gallery Cardiovascular Procedures," LightLab Imaging Technology, printed Sep. 3, 2003.

"Optical Coherence Tomography: What is OCT?," LightLab Imaging Technology, printed Sep. 3, 2003.

"Optical Coherence Tomography: Why Use OCT?," LightLab Imaging Technology, printed Sep. 3, 2003.

\* cited by examiner

ULTRASOUND ABLATION CATHETER WITH COOLING INFUSION AND CENTERING BASKET

CROSS-REFERENCE TO RELATED APPLICATIONS

This application claims priority under 35 U.S.C. §119 to U.S. Provisional Application Ser. No. 61/891,241, filed Oct. 15, 2013, the entirety of which is incorporated herein by reference.

TECHNICAL FIELD

The present disclosure relates generally to systems and methods for nerve modulation techniques such as ablation of nerve tissue or other modulation techniques through the walls of blood vessels.

BACKGROUND

Certain treatments may require the temporary or permanent interruption or modification of selected nerve function. One exemplary treatment is renal nerve ablation, which is sometimes used to treat conditions related to congestive heart failure or hypertension. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Many nerves (and nervous tissue such as brain tissue), including renal nerves, run along the walls of or in close proximity to blood vessels and thus can be accessed intravascularly through the walls of the blood vessels. In some instances, it may be desirable to ablate perivascular nerves using ultrasonic energy. In other instances, the perivascular nerves may be ablated by other means including application of thermal, radiofrequency, laser, microwave, and other related energy sources to the target region. Ultrasound transducers may dissipate some energy as heat into the blood and surrounding tissue as well as causing the ultrasound transducers to become hot. This may result in blood damage, clotting, and/or protein fouling of the transducer among other undesirable side effects. In some instances, overheating of the ultrasound transducer may result in the failure of the transducers.

SUMMARY

The present disclosure is directed to an intravascular nerve modulation system for performing nerve ablation.

Accordingly, one illustrative embodiment includes an intravascular nerve modulation system having a catheter shaft. The catheter shaft may define a first lumen and having a proximal end and a distal end. Further, the system includes a first flexible mount member affixed to the distal end of the catheter shaft and defining one or more through holes. Furthermore, the system includes a cylindrical ablation transducer coupled to the first flexible mount and defining a lumen extending distally from the first flexible mount. Here, the lumen of the catheter shaft, the through holes of the first flexible mount member, and the lumen of the transducer are in fluid communication with one another.

Another illustrative embodiment includes an intravascular nerve modulation system that may include an elongate shaft having a proximal end, a distal end, and a lumen extending therebetween. Further, the system may include an ablation transducer affixed to the elongate shaft adjacent the distal end thereof. Furthermore, the intravascular modulation system may include an expandable basket having a proximal end affixed to the elongate shaft and a distal end affixed to an end cap positioned distal of a distal end of the ablation transducer. Here, the expandable basket may be configured to actuate between a first collapsed configuration and a second expanded configuration. In addition, the expandable basket can include two or more longitudinally extending struts and one or more temperature sensors may be coupled to the expandable basket. The system can further include a pull wire affixed to the end cap such that actuation of the pull wire moves the expandable basket between the first collapsed position and the second expanded position. Alternatively, the expandable basket may be configured to self-expand. The system can further include an infusion sheath secured adjacent to the distal end of the elongate tubular member such that the infusion sheath is configured to extend over the ablation transducer. In some instances, the distal end of the expandable basket may be affixed to the elongate shaft.

Another example intravascular nerve modulation system may include an elongate shaft having a proximal end region and a distal end region. An ablation transducer may be coupled to the distal end region of the shaft. An expandable basket may be coupled to the distal end region of the shaft. The expandable basket may have a proximal end dispsoed proximal of the ablation transducer and a distal end disposed distal of the ablation transducer. The expandable basket may be capable of shifting between a first configuration and an expanded configuration. A sensor may be coupled to the expandable basket.

Another example intravascular nerve modulation system may include an elongate shaft having a proximal end region and a distal end region. An ultrasound transducer may be coupled to the distal end region of the shaft. An expandable basket may be coupled to the distal end region of the shaft. The expandable basket may have a proximal end disposed proximal of the ultrasound transducer and a distal end disposed distal of the ultrasound transducer. The expandable basket may be capable of shifting between a first configuration and an expanded configuration. A sensor may be coupled to the expandable basket. The sensor may be capable of contacting a vessel wall when the basket is in the expanded configuration. The sensor may also be designed to monitor the progress of ablation by the ultrasound transducer during an ablation procedure.

Although discussed with specific reference to use with the renal nerves of a patient, the intravascular nerve modulation systems in accordance with the disclosure may be adapted and configured for use in other parts of the anatomy, such as the nervous system, the circulatory system, or other parts of the anatomy of a patient.

The above summary of an example embodiment is not intended to describe each disclosed embodiment or every implementation of the present disclosure.

BRIEF DESCRIPTION OF THE DRAWINGS

The disclosure may be more completely understood in consideration of the following detailed description of various embodiments in connection with the accompanying drawings, in which.

Figure 1:
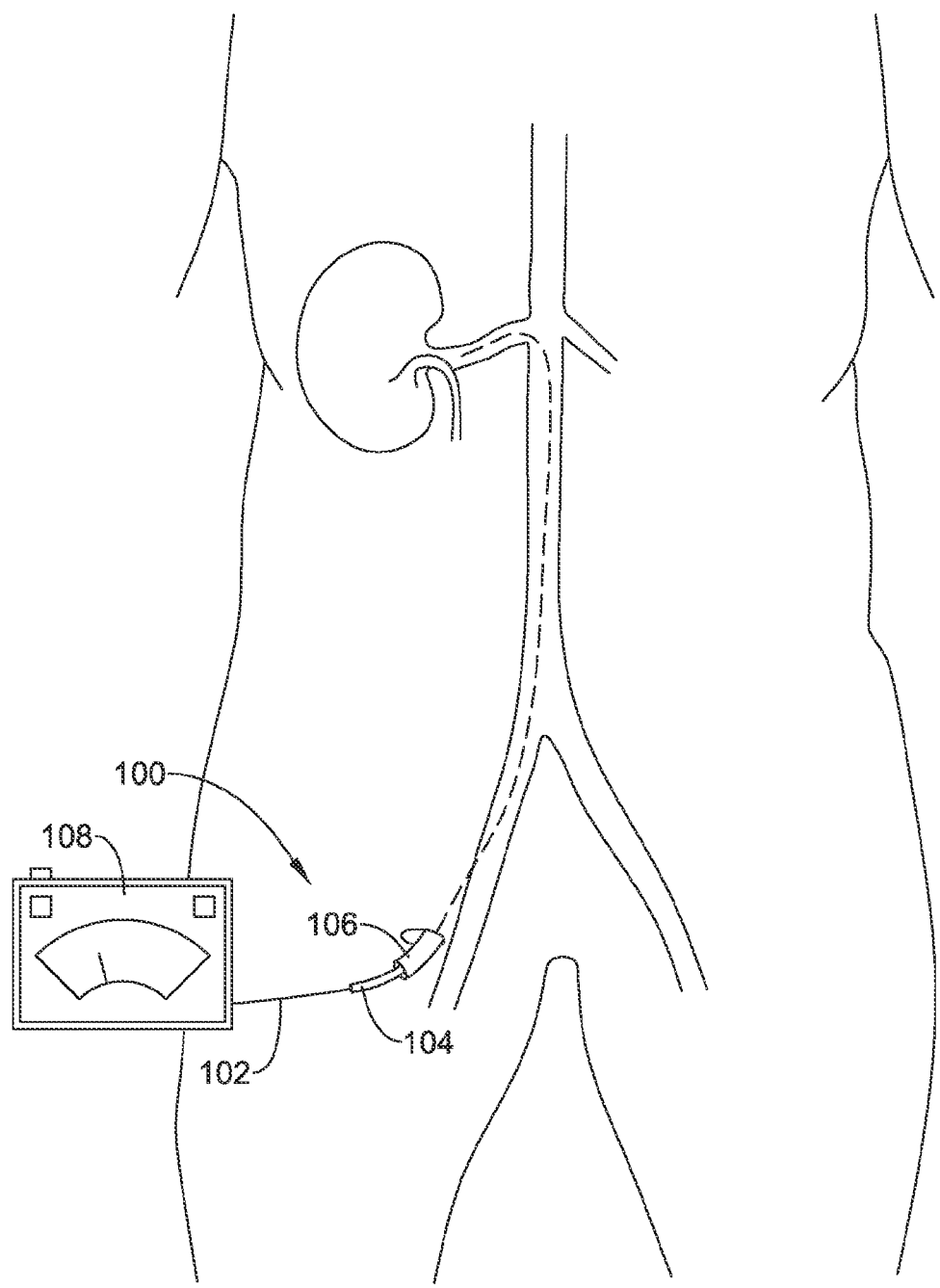
FIG. 1 illustrates an exemplary renal nerve modulation system in situ.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may be indicative as including numbers that are rounded to the nearest significant figure.

The recitation of numerical ranges by endpoints includes all numbers within that range (e.g. 1 to 5 includes 1, 1.5, 2, 2.75, 3, 3.80, 4 , and 5).

Although some suitable dimensions ranges and/or values pertaining to various components, features and/or specifications are disclosed, one of the skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

For purposes of this disclosure, "proximal" refers to the end closer to the device operator during use, and "distal" refers to the end further from the device operator during use.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with one embodiment, it should be understood that such feature, structure, or characteristic may also be used connection with other embodiments whether or not explicitly described unless clearly stated to the contrary.

Certain treatments are aimed at the temporary or permanent interruption or modification of select nerve function. In some instances, the nerves are sympathetic nerves. One example treatment is renal nerve ablation, which is sometimes used to treat conditions related to hypertension, congestive heart failure, diabetes, or other conditions impacted by high blood pressure or salt retention. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Some embodiments of the present disclosure relate to a power generating and control apparatus, often for the treatment of targeted tissue in order to achieve a therapeutic effect. In some embodiments, the target tissue is tissue containing or proximate to nerves. In one embodiment, the target tissue includes renal arteries and associated renal nerves. In other embodiments, the target tissue is sympathetic nerves including, for example, sympathetic nerves disposed adjacent to blood vessels. In still other embodiments the target tissue is luminal tissue, which may further comprise diseased tissue such as that found in arterial disease.

While the systems and methods described herein are discussed relative to renal nerve modulation, it is contemplated that the systems and methods may be used in other locations and/or applications where nerve modulation and/or other tissue modulation including heating, activation, blocking, disrupting, or ablation are desired, such as, but not limited to: blood vessels, urinary vessels, or in other tissues via trocar and cannula access. For example, the devices and methods described herein can be applied to hyperplastic tissue ablation, tumor ablation, benign prostatic hyperplasia therapy, nerve excitation or blocking or ablation, modulation of muscle activity, hyperthermia or other warming of tissues, etc. In some instances, it may be desirable to ablate perivascular renal nerves with ultrasound ablation. The term modulation refers to ablation and other techniques that may alter the function of affected nerves.

Ultrasound energy may be used to generate heat at a target location. The high frequency acoustic waves produced by an ultrasonic transducer may be directed at a target region and absorbed at the target region. As the energy emitted is absorbed, a temperature of the target region may rise. In order to perform renal nerve ablation, target nerves should be heated sufficiently to make them nonfunctional, while thermal injury to the artery wall is undesirable. Heating of the artery wall during the procedure may increase pain, which is also undesirable. When a portion of tissue is ablated, tissue properties change, and increased attenuation of the ultrasound energy can make ablation past this ablated tissue difficult. Ultrasound ablation catheters may also generate significant heat in the ultrasound transducer. That heat may consequently form blood clots on or around the transducer, damage the surrounding blood, and/or damaging the transducers, among other undesirable side effects. As the ablation transducer(s) heat, the energy conversion efficiency of those devices is lowered, thus generating even more heat. Thus, normal operations of ablation transducers may be characterized by increasingly lower efficiency during operation. The efficiency of the ablation transducers may be enhanced using a cooling mechanism. One possible cooling mechanism is passing an infusion fluid over the transducers.

FIG. 1 is a schematic view of an illustrative nerve modulation system 100 in situ. The nerve modulation system 100 may include an element 102 for providing power to a transducer disposed adjacent to, about, and/or within a central elongated shaft 104 and, optionally, within a guide catheter 106. A proximal end of the element 102 may be connected to a power and control element 108, which supplies the necessary electrical energy to activate the one or more transducers at or near a distal end of the element 102. The power and control element 108 may include monitoring elements to monitor parameters such as power, temperature, voltage, pulse size and/or frequency and other suitable parameters as well as suitable controls for performing the desired procedure. In some instances, the control unit 108 may control an ultrasound ablation transducer. The ablation transducer may be configured to operate at a frequency of about 9-10 megahertz (MHz). It is contemplated that any desired frequency may be used, for example, from 1-20 MHz. In addition, it is contemplated that frequencies outside this range may also be used, as desired. While the term "ultrasound" is used herein, this is not meant to limit the range of vibration frequencies contemplated. For example, it is contemplated that the perivascular nerves may be ablated by other means including application of thermal, radiofrequency, laser, microwave, and other related energy sources to the target region.

Figure 2:
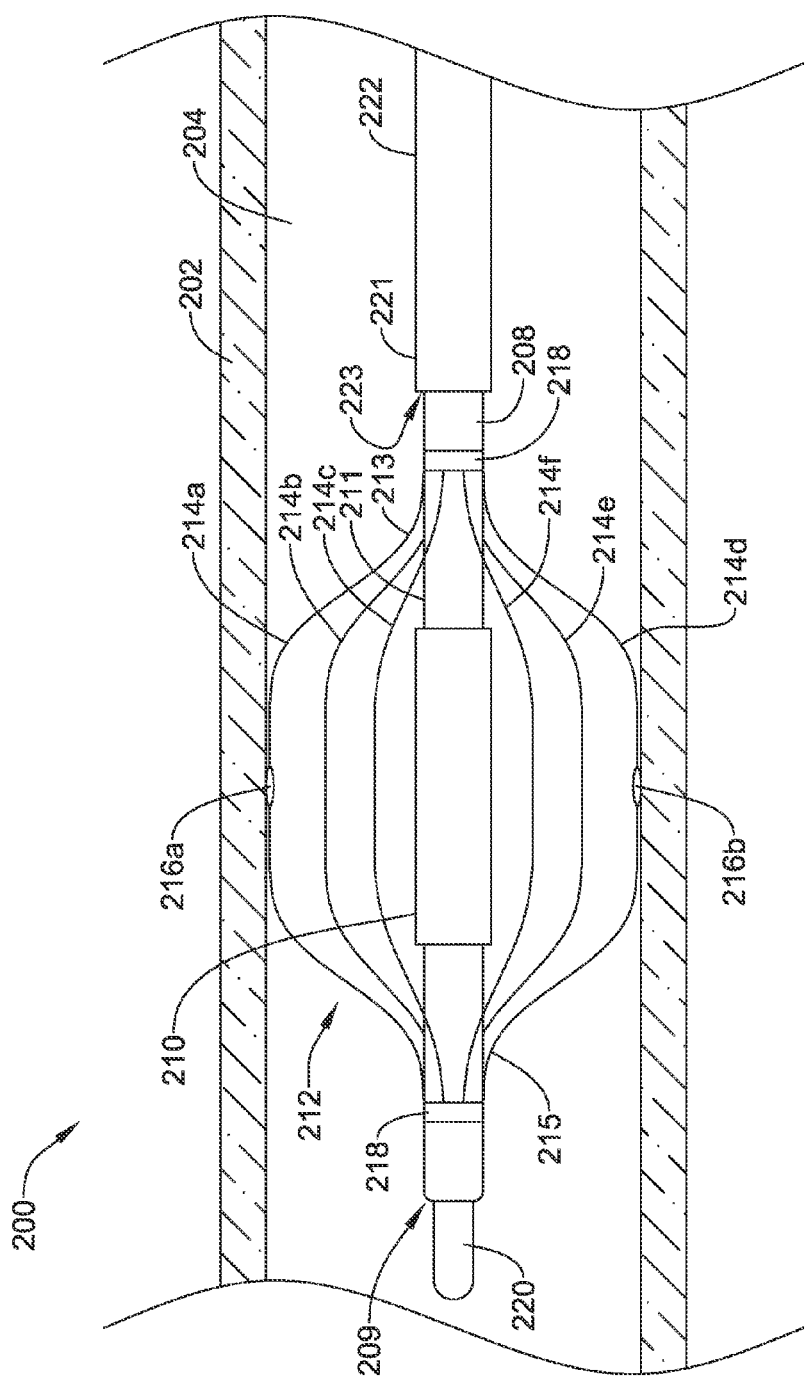
FIG. 2 illustrates a schematic side-view of a portion of an illustrative intravascular nerve modulation system disposed within a body lumen.

FIG. 2 illustrates a schematic side view of a distal end portion of an illustrative intravascular nerve modulation system 200 disposed within a body lumen 204 having a vessel wall 202. Local body tissue (not shown) may surround the vessel wall 202. The local body tissue may comprise adventitia and connective tissues, nerves, fat, fluid, etc., in addition to the muscular vessel wall 202. A portion of the surrounding tissue may constitute the desired treatment region. For instance, one or more renal nerves (not shown) may extend along the outer wall of the body lumen 204.

The system 200 may include an elongate catheter shaft 208 having a proximal end (not shown) and a distal end region 211. The elongate shaft 208 may extend proximally from the distal end region 211 to the proximal end configured to remain outside of a patient's body. Although not shown, the proximal end of the elongate shaft 208 may include a hub attached thereto for connecting other treatment devices or providing a port for facilitating other treatments. It is contemplated that the stiffness of the elongate shaft 208 may be modified to form the modulation system 200 for use in various vessel diameters and various locations within the vascular tree.

In some instances, the elongate shaft 208 may have an elongate tubular structure and may include one or more lumens extending therethrough. For instance, in the illustrated embodiment, the elongate shaft 208 includes a lumen 209 having a guidewire wire 220 slidably disposed therein, however, this is not required. In some embodiments, the elongate shaft may include one or more auxiliary lumens. In some instances, the elongate shaft 208 may include a separate lumen(s) (not shown) for infusion of fluids or for other purposes such as the introduction of a medical device, and so forth. The fluid may facilitate cooling of the modulation system 200 during the ablation procedure, in addition to the cooling of body lumen 204. Further, the lumens may be configured in any way known in the art. For example, the lumen may extend along the entire length of the elongate shaft 208 such as in an over-the-wire catheter or may extend only along a distal portion of the elongate shaft 208 such as in a single operator exchange (SOE) catheter. These examples are not intended to be limiting, but rather examples of some possible configurations. While not explicitly shown, the modulation system 200 may further include temperature sensors/wire, an infusion lumen, radiopaque marker bands, fixed guidewire tip, a guidewire lumen, and/or other components to facilitate the use and advancement of the system 200 within the vasculature.

Further, the elongate shaft 208 may have a relatively long, thin, flexible tubular configuration. In some instances, the elongate shaft 208 may have a generally circular cross-section, however, other suitable configurations such as, but not limited to, rectangular, oval, irregular, or the like may also be contemplated. In addition, the elongate shaft 208 may have a cross-sectional configuration adapted to be received in a desired vessel, such as a renal artery. For instance, the elongate shaft 208 may be sized and configured to accommodate passage through the intravascular path, which leads from a percutaneous access site in, for example, the femoral, brachial, or radial artery, to a targeted treatment site, for example, within a renal artery.

Materials employed to manufacture the elongate shaft 208 may include any suitable biocompatible material. Examples may include metals, polymers, alloys, shape memory materials, etc. Other suitable materials known in the art may also be employed.

The system 200 may further include one or more ablation transducers 210 positioned adjacent the distal end region 211 of the elongate shaft 208. While FIG. 2 illustrates a single ablation transducer 210, it is contemplated that the modulation system 200 may include any number of ablation transducers desired, such as, but not limited to, one, two, three, or more. The ablation transducer 210 is configured to deliver acoustic energy (i.e., ultrasound waves) to the target region around the vessel wall 202. In some instances, the frequency of the ultrasound energy used for the procedure may be set so that the ablated area of tissue starts after it passes through the vessel wall 202 thereby minimizing potential heat damage of the vessel wall 202. While the ablation transducer 210 is described as an ultrasonic transducer, it is contemplated that other methods and devices for raising the temperature of the nerves may be used, such as, but not limited to: radiofrequency, microwave, other acoustic, optical, electrical current, direct contact heating, or other heating.

In some embodiments, the ablation transducer 210 may have a cylindrical shape, however, those skilled in the art will appreciate that any suitable shapes such as, but not limited to, square, rectangular, polygonal, circular, oblong, or the like may also be contemplated. In some instances, such as when a cylindrical transducer is provided, the ablation transducer 210 may extend around the entire circumference of the elongate shaft 208. In an alternative embodiment, however, the ablation transducer 210 may extend partially around the circumference of the elongate shaft 208. For instance, the ablation transducer 210 may include an array of one or more transducers (not shown) positioned about the circumference of the elongate shaft 208. In other embodiments, the ablation transducer 210 may comprise a focused or phased array of transducers. The array may be configured to be directed at a focus region such that multiple transducers are radiating energy at a common target region. It is further contemplated that the ablation transducer 210 may comprise a plurality of longitudinally spaced transducers. Those skilled in the art will appreciate that other suitable configurations of the ablation transducer 210 may also be contemplated without departing from the scope and spirit of the present disclosure.

The ablation transducer 210 may be formed from any suitable material such as, but not limited to, lead zirconate titanate (PZT). It is contemplated that other ceramic or piezoelectric materials may also be used. In some instances, the ablation transducer 210 may include a layer of gold, or other conductive layer, disposed on the acoustically functional areas of the transducer 210 surface for connecting electrical leads to the ablation transducer 210. It is contemplated that the sides/edges of the transducer crystal may be free of conductive material so as not to "short circuit" the transducer 210. In some instances, one or more tie layers may be used to bond the gold to the PZT. For example, a layer of chrome may be disposed between the PZT and the gold to improve adhesion. In other instances, the transducer 210 may include a layer of chrome over the PZT followed by a layer of nickel, and finally a layer of gold. These are just examples. It is contemplated that the layers may be deposited on the PZT using sputter coating, although other deposition techniques may be used as desired.

The ablation transducer 210 may have a radiating surface, and a perimeter surface extending around the outer edge of the ablation transducer 210. The acoustic energy from the radiating surface of the ablation transducer 210 may be transmitted in a spatial pressure distribution related to the shape of the ablation transducer 210. For instance, the cylindrical shape of the ablation transducer 210 may provide a circumferential ablation pattern. In such an instance, the ablation transducer 210 may include a backing layer to direct the acoustic energy in a single direction. In other embodiments, the ablation transducer 210 may be structured to radiate acoustic energy from two radiating surfaces.

In some embodiments, an electrical conductor, such as the element 102 (as shown in FIG. 1), may connect the ablation transducer 210 to a power and control unit (such as control unit 108 in FIG. 1). In some embodiments, the electrical conductor(s) may be disposed within a lumen of the elongate shaft 208. In other embodiments, the electrical conductor(s) may extend along an outside surface of the elongate shaft 208. The electrical conductor(s) may provide electricity to the ablation transducer 210, which may then be converted into acoustic energy. The acoustic energy may be directed from the ablation transducer 210 in a direction generally perpendicular to the radiating surfaces of the transducer 210. As discussed above, acoustic energy radiates from the ablation transducer 210 in a pattern related to the shape of the transducer 210 and lesions formed during ablation take shape similar to contours of the pressure distribution.

The system 200 can further include an expandable frame or basket 212 having a proximal end 213 and a distal end 215. The proximal end 213 of the expandable basket 212 may be affixed to the elongate shaft 208 proximal to the ablation transducer 210 and the distal end 215 may be affixed to elongate shaft 208 distal to the ablation transducer 210. However, it is contemplated that the expandable basket 212 may be positioned along any portion of the elongate shaft 208 desired. The proximal and distal ends 213, 215 of the basket 212 may be affixed to the elongate shaft 208 in any manner desired. For example, in some instances, a band or retaining element 218 may be used to secure the proximal and distal ends 213, 215. In other instances, the proximal and distal ends 213, 215 may be secured to the elongate shaft 208 with an adhesive or other suitable method. It is further contemplated that either or both of the proximal or distal ends 213, 215 may be secured to an element other than the elongate shaft 208 to facilitate expansion and/or contraction of the basket 212.

The expandable basket 212 may include one or more generally longitudinally extending struts 214a 214b, 214c, 214d, 214e, and 214f (collectively referred to hereinafter as struts 214). Although six struts 214 are shown in FIG. 2, it should be noted that any suitable number of struts 214 may be employed for desired purposes. Further, the expandable basket 212 may be configured to actuate between a first collapsed configuration and a second expanded configuration (shown in FIG. 2), which may include transition of the struts 214 from a generally straight configuration to a curved configuration, respectively. More particularly, the struts 214 in the collapsed configuration may extend and/or straighten to be generally parallel with or generally extend along the longitudinal length of the elongate shaft 208. In contrast, in the second expanded configuration, as shown in FIG. 2, the struts 214 may expand and/or curve like the ribs of an umbrella to surround the ablation transducer 210.

According to embodiments of the present disclosure, the expandable basket 212 may be adapted to align and position the ablation transducer 210 within the body lumen 204. In particular, the ultrasound transducer 210 may be positioned at the center of the expandable basket 212 in the expanded configuration. The centering of the ablation transducer 210 may result in better blood flow and accurate ablation geometry. To accomplish this, the expandable basket 212 may expand to meet the vessel wall 202, as discussed above. As shown in FIG. 2, the expandable basket 212 in the second expanded configuration may be arranged and positioned to surround the ablation transducer 210 circumferentially. In such an instance, the expandable basket 212 may facilitate circumferential ablation of the target region while allowing continued blood flow along the lumen 204. Therefore, the expandable basket 212 allows blood flow for cooling and for renal perfusion, unlike occlusive balloon approaches. In some other embodiments, although not shown, the expandable basket 212 may include one or more electrodes or transducers disposed along the struts 214 such as to contact the vessel wall 202, capable of creating one or more lesions during the ablation procedure.

The expandable basket 212 may be self-expandable, or may require external force to expand. A self-expandable basket 212 may be formed of any material or structure that is in a compressed state when force is applied and in an expanded state when force is released. Such material may include, for example, shape memory materials such as Nitinol or any other self-expandable material commonly known in the art. When employing such shape-memory materials, the expandable basket 212 may be heat set in the expanded state and then compressed to fit within a delivery sheath such as a guide sheath 222, for example. Upon reaching the target location within the body lumen 204, the guide sheath 222 can be retracted to deploy the expandable basket 212 in the expanded configuration. In another embodiment, a spring may be provided to effect expansion. Alternatively, external forces such as, but not limited to, pneumatic methods, compressed fluid, or the like may also be employed to expand the expandable basket 212.

In addition, the system 200 may include an actuation mechanism, for example, a pull wire, which may be employed to manipulate or actuate the expandable basket 212 between the collapsed and expanded configurations discussed above. In an embodiment, the pull wire may be attached to the proximal end 213 or distal end 215 of the basket 212 such that a push-pull mechanism of the pull wire may manipulate the expandable basket 212, thus actuating the expandable basket 212 between the collapsed and expanded configurations. To this end, the pull wire may be pulled proximally to pull the expandable basket 212, switching the expandable basket 212 to the expanded configurations. In addition, the pull wire may be pushed distally to switch the expandable basket 212 in the collapsed configuration. Alternatively, the pull wire may be pushed distally, which may allow the expandable basket 212 to move to the expanded state. In such instance, the pull wire may be pulled proximally, which may allow the expandable basket 212 to move to the collapsed state.

The system 200 can further include one or more temperature sensors 216a and 216b (collectively referred hereinafter as sensors 216) coupled to the expandable basket 212. Although two temperature sensors 216 are shown, it should be noted that any suitable number of temperature sensors 216 may employed for desired purposes. In addition, other suitable sensors such as impedance sensors may also be employed. As shown, the temperature sensors 216 may be placed on the struts 214 such as to contact the vessel wall 202 in the expanded configuration. The contact between the sensors 216 and the wall 202 may allow measuring of temperature of the vessel wall 202 during the ablation procedure. According to an example, the temperature sensors 216 may include one or more thermocouples, which may be employed to monitor wall 202 temperatures.

As discussed previously, the system 200 may include one or more guide sheaths 222 having a proximal end (not shown), a distal end 221, and a lumen extending therebetween. It should be noted that guide sheath 222 may include any suitable number of lumens as required or desired. The elongate shaft 208 may be slidably disposed within the lumen of the guide sheath 222. In some instances, the guide sheath 222 may also be used as an infusion sheath. For example, the distal end 221 of the guide sheath 222 may be open to allow an infusion fluid to exit. Saline or other suitable infusion fluid (not shown) may be flushed through the lumen 223. In an alternate embodiment, the infusion fluid may exit through the distal end region 211 of the elongate shaft 208, thereby displacing blood from and around the transducer 210. As the infusion fluid flows past the ablation transducer 210, the infusion fluid may provide convective cooling to the ablation transducer 210. It is further contemplated that by displacing and/or cooling the blood surrounding the transducer 210, blood damage, fouling of the transducer 210, and/or overheating of the transducer 210 may be reduced or eliminated. In some instances, this may allow the modulation system 200 to be operated at a higher power level, thus providing a shorter treatment and/or more effective modulation of the target tissue. In some embodiments, the modulation system may be structured to direct some or all of the infusion fluid along the inside of the vessel wall 202. While blood flowing through the vessel lumen 204 removed some heat from the wall tissue, the addition of a "cooling" flush via infusion fluid directed towards the vessel wall 202 may allow the application of more power for a shorter time period. It is contemplated that the infusion fluid may be introduced into the modulation system 200 before, during, or after ablation. Flow of the infusion fluid may begin before energy is supplied to the ablation transducer 210 and continue for the duration of the modulation procedure. In some instances, a separate infusion sheath (not explicitly shown) may be provided, as will be discussed in more detail below.

The infusion fluid may be saline or any other suitable infusion fluid. It is contemplated that the infusion fluid may be provided at a variety of different temperatures depending on the desired treatment. In some instances, the infusion fluid may be provided at room temperature, below room temperature, above room temperature, or at normal body temperature as desired. In addition, the salinity of the infusion fluid can be chosen to obtain desired electrical conductivity, such as to improve the discrimination capability of impedance monitoring. In some instances, such as when an imaging transducer is provided (not explicitly shown), a small amount of an imaging contrast material may be added to the infusion fluid to facilitate imaging of the vessel. Suitable examples of such imaging contrast material may include, but are not limited to fluorine, iodine, barium, or the like.

The modulation system 200 may be advanced through the vasculature in any manner known in the art. For example, system 200 may include a guidewire lumen to allow the system 200 to be advanced over a previously located guidewire, such as guidewire 220. In some embodiments, the modulation system 200 may be advanced, or partially advanced, within a delivery catheter such as the guide catheter 222. Once the transducer 210 of the modulation system 200 has been placed adjacent to the desired treatment area, positioning mechanisms, such as basket 212, may be deployed, if so provided. The transducer 210 may be connected to a power and control unit (such as control unit 108 in FIG. 1) by an electrical conductor. The transducer 210 may be connected to one or more control units, which may provide and/or monitor the system 200 with one or more parameters such as, but not limited to, frequency for performing the desired ablation procedure as well as imaging. In some embodiments, the electrical conductor may be disposed within a lumen of the elongate shaft 208. In other embodiments, the electrical conductor may be extended along an outside surface of the elongate shaft 208.

Once the modulation system 200 has been advanced to the treatment region, the expandable basket 212 may be moved to the expanded configuration to position and align the transducer 210 within the lumen 204. Further, an infusion fluid may be provided through a lumen of an infusion sheath. It is contemplated that energy may be supplied to the ablation transducer 210 before, during, and/or after the expandable basket 212 is shifted to the expanded configuration. The electrical conductor may provide electricity to the ablation transducer 210, and that energy may then be converted into acoustic energy. The acoustic energy may be directed from the ablation transducer 210 in a direction generally perpendicular to the radiating surfaces of the ablation transducer 210, generally in a pattern related to the shape of the ablation transducer 210. Although FIG. 1 illustrates a single electrical conductor 102, it is contemplated that the modulation system 200 may include any number of electrical conductors desired, such as, but not limited to, two, three, or more. For example, if multiple ablation transducers are provided, multiple electrical conductors may be required. The amount of energy delivered to the transducer 210 may be determined by the desired treatment as well as the feedback provided by monitoring devices, such as sensors 216.

In some instances, such as when a transducer does not extend around the entire circumference of the elongate shaft 208, the elongate shaft 208 may be rotated and additional ablation can be performed at multiple locations around the circumference of the lumen 204. In some instances, a slow automated "rotisserie" rotation can be used to work around the circumference of the lumen 204, or a faster spinning can be used to simultaneously ablate around the entire circumference. The spinning can be accomplished with a distal micro-motor or by spinning a drive shaft from the proximal end. In other instances, the elongate shaft 208 may be indexed incrementally between desired orientations. In some embodiments, temperature sensors 216 can provide information that can be used to selectively turn on and off the ablation transducer 210 to warm any cool spots or accommodate for veins, or other tissue variations. The number of times the elongate shaft 208 is rotated at a given longitudinal location may be determined by the number, size and/or shape of the transducer 210 on the elongate shaft 208. Once a particular location has been ablated, it may be desirable to perform further ablation procedures at different longitudinal locations. Once the elongate shaft 208 has been longitudinally repositioned, energy may once again be delivered to the transducer 210 to perform ablation and/or imaging as desired. If necessary, the elongate shaft 208 may be rotated to perform ablation around the circumference of the lumen 204 at each longitudinal location. This process may be repeated at any number of longitudinal locations desired. It is contemplated that in some embodiments, the system 200 may include multiple transducers 210 located at various positions along the length of the elongate shaft 208 such that a larger region may be treated without longitudinal displacement of the elongate shaft 208.

Figure 3A:
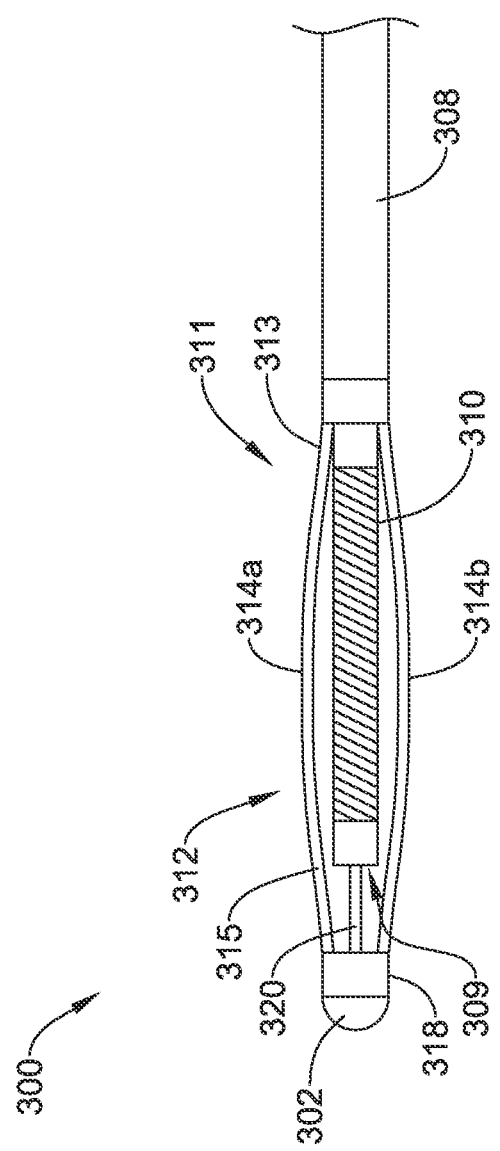
FIG. 3A illustrates a schematic side-view of a portion of another illustrative intravascular nerve modulation system in a collapsed configuration.
Figure 3B:
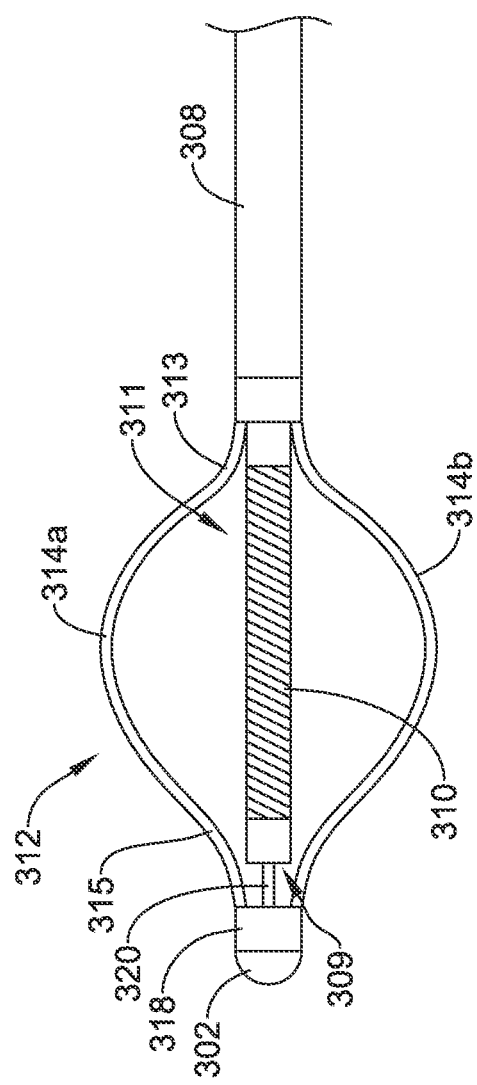
FIG. 3B illustrates a schematic side-view of the intravascular nerve modulation system of FIG. 3A in an expanded configuration.

Referring now to FIGS. 3A and 3B, side views of a distal portion of another illustrative intravascular nerve modulation system 300 is depicted. The system 300 may include an elongate shaft 308 having a proximal end region (not shown), a distal end region 311, and a lumen 309 extending therebetween. The elongate shaft 308 may have similar form and function to the elongate shaft 208 discussed above.

The elongate shaft 308 may extend proximally from the distal end region 311 to the proximal end configured to remain outside of a patient's body. Although not shown, the proximal end of the elongate shaft 308 may include a hub attached thereto for connecting other treatment devices or providing a port for facilitating other treatments. It is contemplated that the stiffness of the elongate shaft 308 may be modified to form the modulation system 300 for use in various vessel diameters and various locations within the vascular tree.

The elongate shaft 308 may include one or more lumens extending therethrough. For instance, in the illustrated embodiment, the elongate shaft 308 may include a lumen 309 having a pull wire 320 slidably disposed therein. In some instances, the elongate shaft 308 may include a separate guidewire lumen and/or separate lumen(s) (not shown) for infusion of fluids or for other purposes such as introduction of a medical device, and so forth. The fluid may facilitate cooling of the modulation system 300 during the ablation procedure. Further, the lumen 309 may be configured in any way known in the art. For example, the lumen 309 may extend along the entire length of the elongate shaft 308 such as in an over-the-wire catheter or may extend only along a distal portion of the elongate shaft 308 such as in a single operator exchange (SOE) catheter. These examples are not intended to be limiting, but rather examples of some possible configurations.

Further, the elongate shaft 308 has a relatively long, thin, flexible tubular configuration. In some instances, the elongate shaft 308 may have a generally circular cross-section, however, other suitable configurations such as, but not limited to, rectangular, oval, irregular, or the like may also be contemplated. In addition, the elongate shaft 308 may have a cross-sectional configuration adapted to be received in a desired vessel, such as a renal artery. For instance, the elongate shaft 308 may be sized and configured to accommodate passage through the intravascular path, which leads from a percutaneous access site in, for example, the femoral, brachial, or radial artery, to a targeted treatment site, for example, within a renal artery.

Materials employed to manufacture the elongate shaft 308 may include any suitable biocompatible material. Examples may include metals, polymers, alloys, shape memory alloys, etc. Other suitable materials known in the art may also be employed.

The system 300 may further include one or more ablation transducers 310 positioned adjacent the distal end region 311 of the elongate shaft 308. While FIGS. 3A and 3B illustrate a single ablation transducer 310, it is contemplated that the modulation system 300 may include any number of ablation transducers desired, such as, but not limited to, one, two, three, or more. The ablation transducer 310 is configured to deliver acoustic energy (i.e., ultrasound waves) to the target region around a vessel wall. At the targeted tissue, the acoustic energy is converted to heat, resulting in protein denaturation and coagulative necrosis of the tissue and/or nerves at the target region. In some instances, the frequency of the ultrasound energy used for the procedure may be set so that the ablated area of tissue starts after it passes through the vessel wall thereby minimizing potential heat damage of the vessel wall. The ablation transducer 310 may be similar in form and function to ablation transducer 210 discussed above.

While the ablation transducer 310 is described as an ultrasonic transducer, it is contemplated that other methods and devices for raising the temperature of the nerves may be used, such as, but not limited to: radiofrequency, microwave, other acoustic, optical, electrical current, direct contact heating, or other heating.

Further, the ablation transducer 310 may have a cylindrical shape, however, those skilled in the art will appreciate that any suitable shapes such as, but not limited to, square, rectangular, polygonal, circular, oblong, or the like may also be contemplated. In some instances, such as when a cylindrical transducer is provided, the ablation transducer 310 may extend around the entire circumference of the elongate tubular member 308. In an alternative embodiment, however, the ablation transducer 310 may extend partially around the circumference of the elongate tubular member 208. For instance, the ablation transducer 310 may include an array of one or more transducers (not shown) positioned about the circumference of the elongate tubular member 308. In other embodiments, the ablation transducer 310 may comprise a focused or phased array of transducers. The array may be configured to be directed at a focus region such that multiple transducers are radiating energy at a common target region. It is further contemplated that the ablation transducer 310 may comprise a plurality of longitudinally spaced transducers. Those skilled in the art will appreciate that other suitable configurations of the ablation transducer 310 may also be contemplated without departing from the scope and spirit of the present disclosure.

The ablation transducer 310 may be formed from any suitable material such as, but not limited to, lead zirconate titanate (PZT). It is contemplated that other ceramic or piezoelectric materials may also be used. In some instances, the ablation transducer 310 may include a layer of gold, or other conductive layer, disposed on the acoustically functional areas of the transducer 310 surface for connecting electrical leads to the ablation transducer 310. It is contemplated that the sides/edges of the transducer crystal may be free of conductive material so as not to "short circuit" the transducer 310. In some instances, one or more tie layers may be used to bond the gold to the PZT. For example, a layer of chrome may be disposed between the PZT and the gold to improve adhesion. In other instances, the transducer 310 may include a layer of chrome over the PZT followed by a layer of nickel, and finally a layer of gold. These are just examples. It is contemplated that the layers may be deposited on the PZT using sputter coating, although other deposition techniques may be used as desired.

Although not shown, the ablation transducer 310 may have a radiating surface, and a perimeter surface extending around the outer edge of the ablation transducer 310. The acoustic energy from the radiating surface of the ablation transducer 310 may be transmitted in a spatial pressure distribution related to the shape of the ablation transducer 310. For instance, the cylindrical shape of the ablation transducer 310 may provide a circumferential ablation pattern. In such an instance, the ablation transducer 310 may include a backing layer to direct the acoustic energy in a single direction. In other embodiments, the ablation transducer 310 may be structured to radiate acoustic energy from two radiating surfaces.

In some embodiments, an electrical conductor such as the element 102 (as shown in FIG. 1) may connect the ablation transducer 310 to a control unit (such as control unit 108 in FIG. 1). In some embodiments, the electrical conductor(s) may be disposed within a lumen of the elongated shaft 308. In other embodiments, the electrical conductor(s) may extend along an outside surface of the elongated shaft 308. The electrical conductor(s) 102 may provide electricity to the ablation transducer 310, which may then be converted into acoustic energy. The acoustic energy may be directed from the ablation transducer 310 in a direction generally perpendicular to the radiating surfaces of the transducer 310. As discussed above, acoustic energy radiates from the ablation transducer 310 in a pattern related to the shape of the transducer 310 and lesions formed during ablation take shape similar to contours of the pressure distribution.

The system 300 can further include an expandable basket 312 having a proximal end 313 and a distal end 315. The proximal end 313 may be affixed adjacent the distal end region 311 of the elongate shaft 308 and the distal end 315 may be affixed to an end cap 318 positioned distal of a distal end of the ablation transducer 310. The end cap 318 may have a rounded distal portion 302, which may avoid any injury to the body tissue while the system 300 is introduced in a body lumen.

The expandable basket 312 may include two (or more) generally longitudinally extending struts 314a and 314b (collectively referred hereinafter as struts 314). Although two struts 314 are visible in FIGS. 3A and 3B, it should be noted that any suitable number of struts 314 may be employed for desired purposes. Further, the expandable basket 312 is configured to actuate between a first collapsed configuration and a second expanded configuration, which may include transition of the struts 314 from a generally straight or slightly bowed configuration (as shown in FIG. 3A) to a curved configuration (as shown in FIG. 3B), respectively. More particularly, the struts 314 in the collapsed configuration may extend and/or straighten to be generally parallel with or generally extend along the longitudinal length of the elongate shaft 308, as shown in FIG. 3A. In contrast, in the second expanded configuration, as shown in FIG. 3B, the struts 314 may expand and/or curve like the ribs of an umbrella to surround the ablation transducer 310. Further, the expandable basket 312 may have similar form and function to the expandable basket 212 discussed above.

According to embodiments of the present disclosure, the expandable basket 312 can be adapted to align and position the ablation transducer 310 within a body lumen. To accomplish this, the expandable basket 312 may expand to meet the vessel wall. As shown in FIG. 3B, the expandable basket 312 may expand to the second expanded configuration, which may be arranged and positioned to contact the vessel wall and may position the ablation transducer 310 approximately in the center of the lumen. In such an instance, the expandable basket 312 may facilitate circumferential ablation of the target region while allowing continued blood flow along the lumen. In some other embodiments, although not shown, the expandable basket 312 may include one or more electrodes or transducers disposed along the struts 314 capable of creating lesion(s) while being in contact with the vessel wall.

In the present embodiment, the expandable basket 312 may include an actuation mechanism for moving the basket 312 between the collapsed and expanded positions. For example, the pull wire 320 may be employed to manipulate or actuate the expandable basket 312 between the collapsed and expanded configurations. In an embodiment, the pull wire 320 may be distally attached to the end cap 318 such that a push-pull mechanism of the pull wire 320 may manipulate the expandable basket 312, thus actuating the expandable basket 312 between the collapsed and expanded configurations, respectively. To this end, the pull wire 320, while being affixed to the end cap 318, may be pulled proximally to pull the expandable basket 312, switching the expandable basket 312 to the expanded configurations, as shown in FIG. 3B. In other embodiments, the pull wire 320 may be affixed to the distal end 315 of the basket 312. In this instance, distal actuation of the pull wire 320 may expand the basket 312.

While not explicitly shown, the system 300 may include one or more temperature sensors coupled to the expandable basket 312. In addition, other suitable sensors such as impedance sensors may also be employed. Contact between the sensors and the lumen wall may allow measuring of temperature of the lumen wall during the ablation procedure. According to an example, the temperature sensors may include one or more thermocouples, which may be employed to monitor wall temperatures.

While not explicitly shown, the system 300 can also include one or more guide sheaths having a proximal end, a distal end, and a lumen extending therebetween. The guide sheath may have similar form and function to the guide sheath 222 as discussed above. The elongate shaft 308 may be slidably disposed within the lumen of the guide sheath. In some instances, the guide sheath may also be used as an infusion sheath. For example, the distal end of the guide sheath may be open to allow an infusion fluid to exit. Saline or other suitable infusion fluid (not shown) may be flushed through the lumen.

In an alternate embodiment, an infusion fluid may exit through the distal end region 311 of the elongate shaft 308, thereby displacing blood from and around the transducer 310. As the infusion fluid flows past the ablation transducer 310, the infusion fluid may provide convective cooling to the ablation transducer 310. It is further contemplated that by displacing and/or cooling the blood surrounding the transducer 310, blood damage, fouling of the transducer 310, and/or overheating of the transducer 310 may be reduced or eliminated. In some instances, this may allow the modulation system 300 to be operated at a higher power level, thus providing a shorter treatment and/or more effective modulation of the target tissue. In some embodiments, the modulation system 300 may be structured to direct some or all of the infusion fluid along the inside of the vessel wall. While blood flowing through the vessel lumen removed some heat from the wall tissue, the addition of a "cooling" flush via infusion fluid directed towards the vessel wall may allow the application of more power for a shorter time period. It is contemplated that the infusion fluid may be introduced into the modulation system 300 before, during, or after ablation. Flow of the infusion fluid may begin before energy is supplied to the ablation transducer 310 and continue for the duration of the modulation procedure. In some instances, a separate infusion sheath (not explicitly shown) may be provided, as will be discussed in more detail below.

Although not shown, the modulation system 300 may further include radiopaque marker bands, fixed guidewire tip, a guidewire lumen, and/or other components to facilitate the use and advancement of the system 300 within the vasculature. In addition, the system 300 can further include one or more sensors (e.g. temperature, impedance, etc.) for monitoring the ablation procedure. It should be noted that any suitable number of temperature sensors may employed for desired purposes. In addition, other suitable sensors such as impedance sensors may also be employed.

Figure 4:
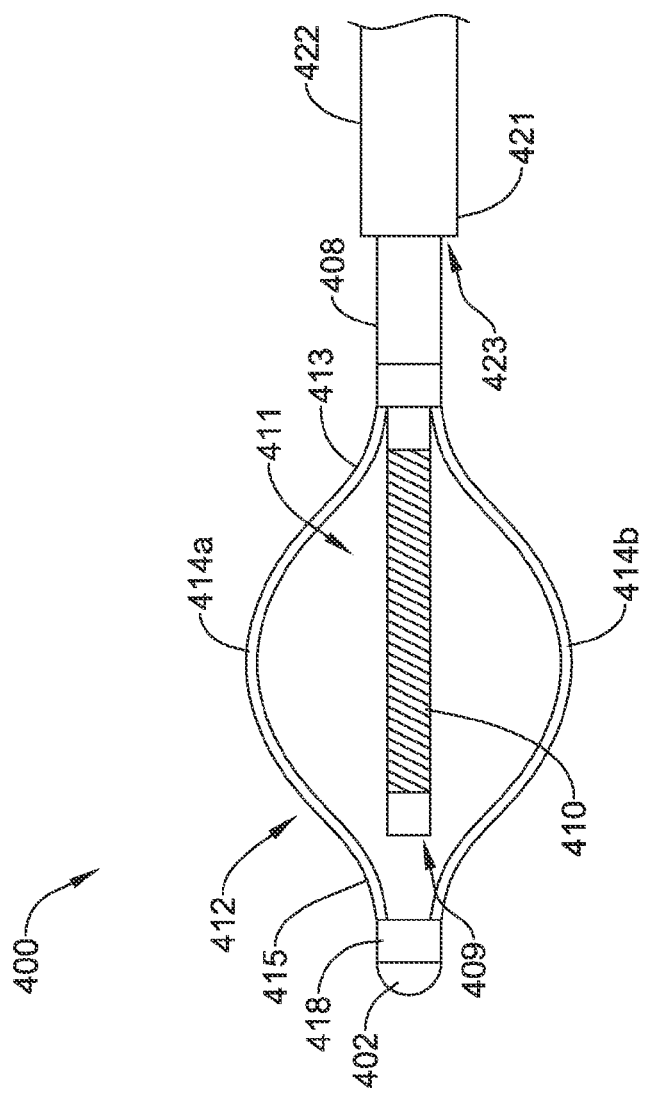
FIG. 4 illustrates a schematic side-view of a portion of another illustrative intravascular nerve modulation system.

Turning now to FIG. 4, a side view of a distal portion of another illustrative intravascular nerve modulation system 400 is depicted. The system 400 may include an elongate shaft 408 having a proximal end (not shown), a distal end region 411, and a lumen 409 extending therebetween. The elongate shaft 408 may extend proximally from the distal end region 411 to the proximal end configured to remain outside of a patient's body. Although not shown, the proximal end of the elongate shaft 408 may include a hub attached thereto for connecting other treatment devices or providing a port for facilitating other treatments. It is contemplated that the stiffness of the elongate shaft 408 may be modified to form the modulation system 400 for use in various vessel diameters and various locations within the vascular tree. The elongate shaft 408 may be similar in form and function to elongate shafts 208, 308 discussed above.

The elongate shaft 408 may include one or more lumens extending therethrough. For instance, in the illustrated embodiment, the elongate shaft 408 may include a lumen 409 for receiving a guidewire therethrough. In some instances, the elongate shaft 408 may include a separate guidewire lumen and/or separate lumen(s) (not shown) for infusion of fluids or for other purposes such as introduction of a medical device, and so forth. The fluid may facilitate cooling of the modulation system 400 during the ablation procedure. Further, the lumen 409 may be configured in any way known in the art. For example, the lumen 409 may extend along the entire length of the elongate shaft 408 such as in an over-the-wire catheter or may extend only along a distal portion of the elongate shaft 408 such as in a single operator exchange (SOE) catheter. These examples are not intended to be limiting, but rather examples of some possible configurations. Further, the elongate shaft 408 has a relatively long, thin, flexible tubular configuration. In some instances, the elongate shaft 408 may have a generally circular cross-section, however, other suitable configurations such as, but not limited to, rectangular, oval, irregular, or the like may also be contemplated. In addition, the elongate shaft 408 may have a cross-sectional configuration adapted to be received in a desired vessel, such as a renal artery. For instance, the elongate shaft 408 may be sized and configured to accommodate passage through the intravascular path, which leads from a percutaneous access site in, for example, the femoral, brachial, or radial artery, to a targeted treatment site, for example, within a renal artery.

Materials employed to manufacture the elongate shaft 408 may include any suitable biocompatible material. Examples may include metals, polymers, alloys, shape memory alloys, etc. Other suitable materials known in the art may also be employed.

The system 400 can further include one or more ablation transducers 410 positioned adjacent the distal end region 411 of the elongate shaft 408. While FIG. 4 illustrates single ablation transducer 410, it is contemplated that the modulation system 400 may include any number of ablation transducers desired, such as, but not limited to, one, two, three, or more. The ablation transducer 410 is configured to deliver acoustic energy (i.e., ultrasound waves) to the target region around the vessel wall. At the targeted tissue, the acoustic energy is converted to heat resulting in protein denaturation and coagulative necrosis of the tissue and/or nerves at the target region. In some instances, the frequency of the ultrasound energy used for the procedure may be set so that the ablated area of tissue starts after it passes through the vessel wall thereby minimizing potential heat damage of the vessel wall. The ablation transducer 410 may be similar in form and function to ablation transducers 210, 310 discussed above.

While the ablation transducer 410 is described as an ultrasonic transducer, it is contemplated that other methods and devices for raising the temperature of the nerves may be used, such as, but not limited to: radiofrequency, microwave, other acoustic, optical, electrical current, direct contact heating, or other heating.

Further, the ablation transducer 410 may have a cylindrical shape, however, those skilled in the art will appreciate that any suitable shapes such as, but not limited to, square, rectangular, polygonal, circular, oblong, or the like may also be contemplated. In some instances, such as when a cylindrical transducer is provided, the ablation transducer 410 may extend around the entire circumference of the elongate tubular member 408. In an alternative embodiment, however, the ablation transducer 410 may extend partially around the circumference of the elongate tubular member 408. For instance, the ablation transducer 410 may include an array of one or more transducers (not shown) positioned about the circumference of the elongate tubular member 408. In other embodiments, the ablation transducer 410 may comprise a focused or phased array of transducers. The array may be configured to be directed at a focus region such that multiple transducers are radiating energy at a common target region. It is further contemplated that the ablation transducer 410 may comprise a plurality of longitudinally spaced transducers. Those skilled in the art will appreciate that other suitable configurations of the ablation transducer 410 may also be contemplated without departing from the scope and spirit of the present disclosure.

The ablation transducer 410 may be formed from any suitable material such as, but not limited to, lead zirconate titanate (PZT). It is contemplated that other ceramic or piezoelectric materials may also be used. In some instances, the ablation transducer 410 may include a layer of gold, or other conductive layer, disposed on the acoustically functional areas of the transducer 410 surface for connecting electrical leads to the ablation transducer 410. It is contemplated that the sides/edges of the transducer crystal may be free of conductive material so as not to "short circuit" the transducer 410. In some instances, one or more tie layers may be used to bond the gold to the PZT. For example, a layer of chrome may be disposed between the PZT and the gold to improve adhesion. In other instances, the transducer 210 may include a layer of chrome over the PZT followed by a layer of nickel, and finally a layer of gold. These are just examples. It is contemplated that the layers may be deposited on the PZT using sputter coating, although other deposition techniques may be used as desired.

Although not shown, the ablation transducer 410 may have a radiating surface, and a perimeter surface extending around the outer edge of the ablation transducer 410. The acoustic energy from the radiating surface of the ablation transducer 410 may be transmitted in a spatial pressure distribution related to the shape of the ablation transducer 410. For instance, the cylindrical shape of the ablation transducer 410 may provide a circumferential ablation pattern. In such an instance, the ablation transducer 410 may include a backing layer to direct the acoustic energy in a single direction. In other embodiments, the ablation transducer 410 may be structured to radiate acoustic energy from two radiating surfaces.

In some embodiments, an electrical conductor such as the element 102 (as shown in FIG. 1) may connect the ablation transducer 410 to a control unit (such as control unit 108 in FIG. 1). In some embodiments, the electrical conductor(s) may be disposed within a lumen of the elongated shaft 408. In other embodiments, the electrical conductor(s) may extend along an outside surface of the elongated shaft 408. The electrical conductor(s) may provide electricity to the ablation transducer 410, which may then be converted into acoustic energy. The acoustic energy may be directed from the ablation transducer 410 in a direction generally perpendicular to the radiating surfaces of the transducer 410. As discussed above, acoustic energy radiates from the ablation transducer 410 in a pattern related to the shape of the transducer 410 and lesions formed during ablation take shape similar to contours of the pressure distribution.

The system 400 can further include an expandable basket 412 having a proximal end 413 and a distal end 415. The proximal end 413 of the expandable basket 412 may be affixed adjacent the distal end region 411 of the elongate shaft 408 and the distal end 415 may be affixed to an end cap 418 positioned distal of a distal end of the ablation transducer 410. The end cap 418 may have a rounded distal portion 402, which may avoid any injury to the body tissue while the system 400 is introduced in a body lumen.

The expandable basket 412 may include two (or more) generally longitudinally extending struts 414a and 414b (collectively referred hereinafter as struts 414). Although two struts 414 are visible in FIG. 4, it should be noted that any suitable number of struts 414 may be employed for desired purposes. Further, the expandable basket 412 is configured to actuate between a first collapsed configuration and a second expanded configuration, which may include transition of the struts 414 from a generally straight or slightly bowed configuration to a curved configuration (shown in FIG. 4), respectively. More particularly, the struts 414 in the collapsed configuration may extend and/or straighten generally parallel (not explicitly shown) along the longitudinal length of the elongate shaft 408 similar to struts 314 shown in FIG. 3A. In contrast, in the second expanded configuration (shown in FIG. 4), the struts 414 may expand and/or curve like the ribs of an umbrella to surround the ablation transducer 410. Further, the expandable basket 412 may have similar form and function to the expandable baskets 212, 312 discussed above.

According to embodiments of the present disclosure, the expandable basket 412 can be adapted to align and position the ablation transducer 410 within a body lumen. To accomplish this, the expandable basket 412 may expand to meet the vessel wall. As shown in FIG. 4, the expandable basket 412 may expand to the second expanded configuration, which may be arranged and positioned to contact the vessel wall and may position the ablation transducer 410 approximately in the center of the lumen. In such an instance, the expandable basket 412 may facilitate circumferential ablation of the target region while allowing continued blood flow along the lumen. In some other embodiments, although not shown, the expandable basket 412 may include one or more electrodes or transducers disposed along the struts 414 capable of creating lesion(s) while being in contact with the vessel wall, or to monitor temperature or other characteristics.

In present embodiment, the expandable basket 412 may be self-expandable and may not require external force to expand. Self-expandable expandable basket 412 may be formed of any material or structure that is in a compressed state when force is applied and in an expanded state when force is released. Such material may include, for example, shape memory alloys such as Nitinol or any other self-expandable material commonly known in the art. When employing such shape-memory materials, the expandable basket 412 may be heat set in the expanded state and then compressed to fit within a delivery sheath such as a guide sheath 422, for example. Upon reaching the target location within the body lumen, the infusion sheath 422 can be retracted proximally to deploy the expandable basket 412 in the expanded configuration. In some embodiment, a spring may be provided to effect expansion. Alternatively, external forces such as, but not limited to, pneumatic methods, compressed fluid, or the like may also be employed to expand the expandable basket 412.

Although not shown, the system 400 may include one or more temperature or other suitable sensors coupled to the expandable basket 412. Other suitable sensors may include impedance sensors or other sensors for monitoring the ablation procedure. According to an example, the sensors may be placed on the struts 414 such as to contact the vessel wall in the expanded configuration. The contact between the sensors and the wall may allow for measuring of temperature or other expected physiological parameter of the vessel wall during the ablation procedure. For example, the temperature sensor may include one or more thermocouple, which may be employed to monitor wall temperatures.

In some embodiments, ultrasound imaging may be used to monitor the ablation procedure. It is contemplated that ultrasound imaging may be used to monitor changes deeper in the tissue and adjust the therapy parameter as needed during the ablation procedure. In some instances, this may allow for the identification of nearby vessels that could be removing heat from the targeted tissue around it, thereby allowing increased power delivery, and thus increased heating, to be concentrated in the targeted location.

As discussed above, the system 400 may include a guide sheath 422 having a proximal end (not shown), a distal end 421, and a lumen 423 extending therebetween. The guide sheath may have similar form and function to the guide sheath 222 as discussed above. The elongate shaft 408 may be slidably disposed within the lumen 423 of the guide sheath 422. In some instances, the guide sheath 422 may also be used as an infusion sheath. For example, the distal end 421 of the guide sheath 422 may be open to allow an infusion fluid to exit. Saline or other suitable infusion fluid (not shown) may be flushed through the lumen.

In an alternate embodiment, an infusion fluid may exit through the distal end region 411 of the elongate shaft 408, thereby displacing blood from and around the transducer 410. As the infusion fluid flows past the ablation transducer 410, the infusion fluid may provide convective cooling to the ablation transducer 410. It is further contemplated that by displacing and/or cooling the blood surrounding the transducer 410, blood damage, fouling of the transducer 410, and/or overheating of the transducer 410 may be reduced or eliminated. In some instances, this may allow the modulation system 400 to be operated at a higher power level, thus providing a shorter treatment and/or more effective modulation of the target tissue. In some embodiments, the modulation system 400 may be structured to direct some or all of the infusion fluid along the inside of the vessel wall. While blood flowing through the vessel lumen removed some heat from the wall tissue, the addition of a "cooling" flush via infusion fluid directed towards the vessel wall may allow the application of more power for a shorter time period. It is contemplated that the infusion fluid may be introduced into the modulation system 400 before, during, or after ablation. Flow of the infusion fluid may begin before energy is supplied to the ablation transducer 410 and continue for the duration of the modulation procedure. In some instances, a separate infusion sheath (not explicitly shown) may be provided, as will be discussed in more detail below.

While not explicitly shown, the modulation system 400 may further include radiopaque marker bands, guidewire, a guidewire lumen, and/or other components to facilitate the use and advancement of the system 400 within the vasculature.

Figure 5:
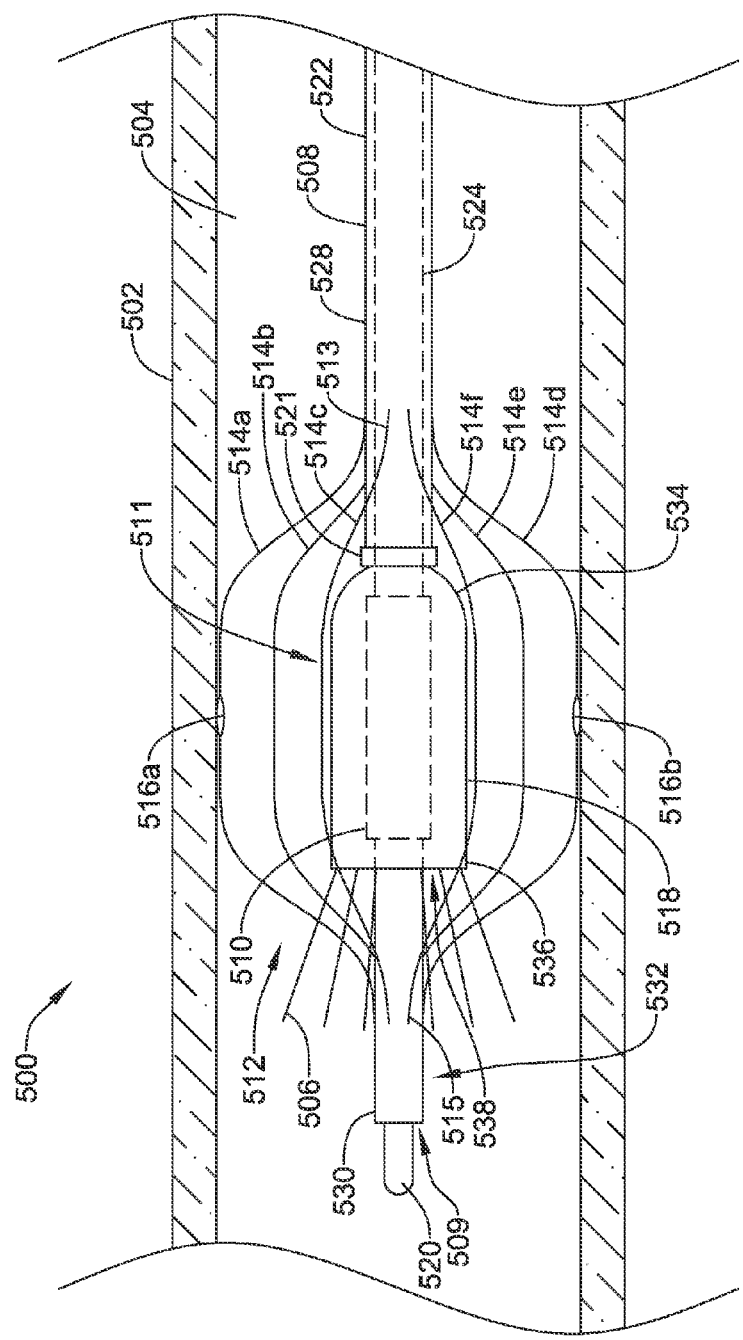
FIG. 5 illustrates a schematic side-view of a portion of another example of an intravascular nerve modulation system disposed within a body lumen.

FIG. 5 illustrates a side view of a distal portion of another example of an intravascular nerve modulation system 500. The system 500 is disposed within a body lumen 504 having a vessel wall 502 surrounded by local body tissue (not shown). The local body tissue may comprise adventitia and connective tissues, nerves, fat, fluid, etc., in addition to the muscular vessel wall 502. A portion of the surrounding tissue may constitute the desired treatment region. For instance, one or more renal nerves (not shown) may extend substantially longitudinally along the outer wall of the body lumen 504.

The system 500 may include an elongate shaft 508 having a distal end region 511. The elongate shaft 508 may extend proximally from the distal end region 511 to a proximal end configured to remain outside of a patient's body. The proximal end of the elongate shaft 508 may include a hub attached thereto for connecting other treatment devices or providing a port for facilitating other treatments. It is contemplated that the stiffness of the elongate shaft 508 may be modified to form a modulation system 500 for use in various vessel diameters and various locations within the vascular tree. The elongate shaft 508 may further include one or more lumens extending therethrough. For example, the elongate shaft 508 may include a guidewire lumen and/or one or more auxiliary lumens. In some instances, the elongate shaft 508 may include an infusion lumen, as will be discussed in more detail below. The lumens may be configured in any way known in the art. For example, the guidewire lumen may extend the entire length of the elongate shaft 508 such as in an over-the-wire catheter or may extend only along a distal portion of the elongate shaft 508 such as in a single operator exchange (SOE) catheter. These examples are not intended to be limiting, but rather examples of some possible configurations. While not explicitly shown, the modulation system 500 may further include temperature sensors/wire, an infusion lumen, radiopaque marker bands, fixed guidewire tip, a guidewire lumen, external sheath, centering basket, and/or other components to facilitate the use and advancement of the system 500 within the vasculature.

In some embodiments, the elongated catheter shaft 508 may have a relatively long, thin, flexible tubular configuration. In some instances, the elongated shaft 508 may have a generally circular cross-section, however, other suitable configurations such as, but not limited to, rectangular, oval, irregular, or the like may also be contemplated. In addition, the elongated shaft 508 may have a cross-sectional configuration adapted to be received in a desired vessel, such as a renal artery. For instance, the elongated shaft 508 may be sized and configured to accommodate passage through the intravascular path, which leads from a percutaneous access site in, for example, the femoral, brachial, or radial artery, to a targeted treatment site, for example, within a renal artery. Materials employed to manufacture the elongate shaft 508 may include any suitable biocompatible material. Examples may include metals, polymers, alloys, shape memory alloys, etc. Other suitable materials known in the art may also be employed.

The elongated shaft 508 may include a first tubular member 522 and a second tubular member 524. The first tubular member 522 may have a proximal end (not shown), a distal end 521 and a lumen 528 extending between the proximal end and the distal end. In some embodiments, the lumen 528 may be an infusion lumen and may be in fluid communication with an infusion fluid source configured to remain outside of a patient's body. The second tubular member 524 may have a proximal end (not shown), a distal end 530, and a lumen 509 extending therebetween. In some embodiments, the lumen 509 of the second tubular member may be a guidewire lumen for receiving a guidewire 520 therein. The distal end region 532 of the second tubular member 524 extends distally beyond the distal end 521 of the first tubular member 522. In some embodiments, the second tubular member 524 may be disposed within or partially within the lumen 528 of first tubular member 522. In some instances, the second tubular member 524 may be coaxially disposed within the first tubular member 522. In other instances, the longitudinal axis of the second tubular member 524 may be offset from the first tubular member 522. In some instances, the first tubular member 522 and the second tubular member 524 may be advanced through the vasculature together.

In addition, the system 500 may include one or more ablation transducers 510 positioned adjacent to the distal end region 532 of the second tubular member 524. While the ablation transducer 510 is shown and described as being positioned on the second tubular member 524, it is contemplated that in some instances, ablation transducers may be provided on the first tubular member 522. While FIG. 5 illustrates one ablation transducer 510, it is contemplated that the modulation system 500 may include any number of ablation transducers desired, such as, but not limited to, one, two, three, or more.

The ablation transducer 510 is configured to deliver acoustic energy (i.e., ultrasound waves) to the target region around the vessel wall 502. At the targeted tissue, the acoustic energy is converted to heat resulting in protein denaturation and coagulative necrosis of the tissue and/or nerves at the target region. In some instances, the frequency of the ultrasound energy used for the procedure may be set so that the ablated area of tissue starts after it passes through the vessel wall 502 thereby minimizing potential heat damage of the vessel wall 502.

While the ablation transducer 510 is described as an ultrasonic transducer, it is contemplated that other methods and devices for raising the temperature of the nerves may be used, such as, but not limited to: radiofrequency, microwave, other acoustic, optical, electrical current, direct contact heating, or other heating.

Further, the ablation transducer 510 may have a cylindrical shape, however, those skilled in the art will appreciate that any suitable shapes such as, but not limited to, square, rectangular, polygonal, circular, oblong, or the like may also be contemplated. In some instances, such as when a cylindrical transducer is provided, the ablation transducer 510 may extend around the entire circumference of the elongate shaft 508. In an alternative embodiment, however, the ablation transducer 510 may extend partially around the circumference of the elongate shaft 508. For instance, the ablation transducer 510 may include an array of one or more transducers (not shown) positioned about the circumference of the elongate shaft 508. In other embodiments, the ablation transducer 510 may comprise a focused or phased array of transducers. The array may be configured to be directed at a focus region such that multiple transducers are radiating energy at a common target region. It is further contemplated that the ablation transducer 510 may comprise a plurality of longitudinally spaced transducers. Those skilled in the art will appreciate that other suitable configurations of the ablation transducer 510 may also be contemplated without departing from the scope and spirit of the present disclosure.

The ablation transducer 510 may be formed from any suitable material such as, but not limited to, lead zirconate titanate (PZT). It is contemplated that other ceramic or piezoelectric materials may also be used. In some instances, the ablation transducer 510 may include a layer of gold, or other conductive layer, disposed on the acoustically functional areas of the transducer 510 surface for connecting electrical leads to the ablation transducer 510. It is contemplated that the sides/edges of the transducer crystal may be free of conductive material so as not to "short circuit" the transducer 510. In some instances, one or more tie layers may be used to bond the gold to the PZT. For example, a layer of chrome may be disposed between the PZT and the gold to improve adhesion. In other instances, the transducer 510 may include a layer of chrome over the PZT followed by a layer of nickel, and finally a layer of gold. These are just examples. It is contemplated that the layers may be deposited on the PZT using sputter coating, although other deposition techniques may be used as desired.

Although not shown, the ablation transducer 510 may have a radiating surface, and a perimeter surface extending around the outer edge of the ablation transducer 510. The acoustic energy from the radiating surface of the ablation transducer 510 may be transmitted in a spatial pressure distribution related to the shape of the ablation transducer 510. For instance, the cylindrical shape of the ablation transducer 510 may provide a circumferential ablation pattern. In such an instance, the ablation transducer 510 may include a backing layer to direct the acoustic energy in a single direction. In other embodiments, the ablation transducer 510 may be structured to radiate acoustic energy from two radiating surfaces.

In some embodiments, an electrical conductor such as the element 102 (as shown in FIG. 1) may connect the ablation transducer 510 to a control unit (such as control unit 108 in FIG. 1). In some embodiments, the electrical conductor(s) may be disposed within a lumen of the elongated shaft 508. In other embodiments, the electrical conductor(s) may extend along an outside surface of the elongated shaft 508. The electrical conductor(s) may provide electricity to the ablation transducer 510, which may then be converted into acoustic energy. The acoustic energy may be directed from the ablation transducer 510 in a direction generally perpendicular to the radiating surfaces of the transducer 510. As discussed above, acoustic energy radiates from the ablation transducer 510 in a pattern related to the shape of the transducer 510 and lesions formed during ablation take shape similar to contours of the pressure distribution.

The system 500 can further include an expandable frame or basket 512 having a proximal end 513 and a distal end 515. The proximal end 513 of the basket 512 may be affixed to the elongate shaft 508 proximal to the transducer 510. In some instances, the proximal end 513 of the basket 512 may be secured to the first tubular member 522, although this is not required. The distal end 515 of the basket 512 may be affixed to the elongate shaft 508 distal to the transducer 510. In some instances, the distal end 515 of the basket 512 may be secured to the second tubular member 524, although this is not required. The proximal and distal ends 513, 515 of the basket 512 may be affixed to the elongate shaft 508 in any manner desired. For example, in some instances, a band or retaining element may be used to secure the proximal and distal ends 513, 515. In other instances, the proximal and distal ends 513, 515 may be secured to the elongate shaft 508 with an adhesive or other suitable method. It is further contemplated that either or both of the proximal or distal ends 513, 515 may be secured to an element other than the elongate shaft 508 to facilitate expansion and/or contraction of the basket 512.

The expandable basket 512 may include one or more longitudinally extending struts 514a, 514b, 514c, 514d, 514e, and 514f (collectively referred to hereinafter as struts 514). Although six struts 514 are shown in FIG. 5, it should be noted that any suitable number of struts 514 may be employed for desired purposes. Further, the expandable basket 512 may be configured to actuate between a first collapsed configuration and a second expanded configuration (shown in FIG. 5), which may include transition of the struts 514 from a generally straight configuration to a curved configuration, respectively. More particularly, the struts 514 in the collapsed configuration may extend and/or straighten to be generally parallel with or generally extend along the longitudinal length of the elongate shaft 508. In contrast, in the second expanded configuration, the struts 514 may expand and/or curve like the ribs of an umbrella to surround the ablation transducer 510.

According to embodiments of the present disclosure, the expandable basket 512 is adapted to align and position the ablation transducer 510 within the body lumen 504. To accomplish this, the expandable basket 512 may expand to meet the vessel wall 502, as discussed above. As shown in FIG. 5, the expandable basket 512 in the second expanded configuration may be arranged and positioned to generally surround the ablation transducer 510 circumferentially to approximately center the ablation transducer 510 within the lumen 504. In such an instance, the expandable basket 512 may facilitate circumferential ablation of the target region while allowing continued blood flow along the lumen 504. In some other embodiments, although not shown, the expandable basket 512 may include one or more electrodes, sensors, or transducers disposed along the struts 514 such as to contact the vessel wall 502, thereby monitoring a particular characteristic or creating one or more lesions during the ablation procedure.

The expandable basket 512 may be self-expandable, or may require external force to expand. A self-expandable expandable basket 512 may be formed of any material or structure that is in a compressed state when force is applied and in an expanded state when force is released. Such material may include, for example, shape memory alloys such as Nitinol or any other self-expandable material commonly known in the art. When employing such shape-memory materials, the expandable basket 512 may be heat set in the expanded state and then compressed to fit within a delivery sheath such as a guide sheath (not explicitly shown), for example. Upon reaching the target location within the body lumen 504, the guide sheath can be retracted to deploy the expandable basket 512 in the expanded configuration. The guide sheath may have similar form and function to the guide sheath 222 as shown in FIG. 2.

In addition, the system 500 may include an actuation mechanism, for example, a pull wire, which may be employed to manipulate or actuate the expandable basket 512 between the collapsed and expanded configurations discussed above. Although not shown, an actuation element such as a wire may be attached to the proximal end 513 or distal end 515 of the expandable basket 512 such that a push-pull mechanism of the wire may manipulate the expandable basket 512, thus actuating the expandable basket 512 between the collapsed and expanded configurations, respectively. In some instances, the wire may be pulled proximally to compress the length of expandable basket 512, switching the expandable basket 512 to the expanded configurations. In addition, the wire may be pushed distally to elongate the expandable basket 512 into the collapsed configuration. Alternatively, the wire may be pushed distally, compress the length of the expandable basket 512 thus expanding the struts 514 into the expanded state. In such an instance, the wire may be pulled proximally, which may allow the expandable basket 512 to elongate the basket 512 into the collapsed state.

The system can further include one or more temperature sensors 516a and 516b (collectively referred to hereinafter as sensors 516) coupled to the expandable basket 512. Although two temperature sensors 516 are shown, it should be noted that any suitable number of temperature sensors 516 may employed for desired purposes. In addition, other suitable sensors, such as impedance sensors, may also be employed. As shown, the temperature sensors 516 may be placed on the struts 514 such as to contact the vessel wall 502 in the expanded configuration. The contact between the sensors 516 and the wall 502 may allow measuring of temperature of the vessel wall 502 during the ablation procedure. According to an example, the temperature sensors 516 may include one or more thermocouple, which may be employed to monitor wall 502 temperatures.

Further, the system 500 may include one or more infusion sheaths 518 having a proximal end 534, a distal end 536 and a lumen 538 extending therethrough. In some embodiments, the proximal end 534 of the infusion sheath 518 may be secured to the catheter shaft 508 adjacent to the distal end 521 of the first tubular member 522. It is contemplated that the infusion sheath 518 may be attached either temporarily or permanently to the catheter shaft 508. Suitable attachment means may include adhesives, heat shrinking, or other suitable means known to those skilled in the art. The distal end 536 of the infusion sheath 518 may be open to allow an infusion fluid 506 to exit the sheath 518. The infusion sheath 518 may be configured to extend distally from the distal end 521 of the first tubular member 522 such that a portion of the distal end region 532 of the second tubular member 524 is disposed within or partially within the lumen 538 of the infusion sheath 518. In some instances, the distal end 530 of the second tubular member 524 may extend beyond the distal end 536 of the infusion sheath 518, but this is not required. In some instances, the ablation transducer 510 may be disposed within or partially within the lumen 538 of the infusion sheath 518, although this is not required. In some instances, the lumen 538 of the infusion sheath may be in fluid communication with the lumen 528 of the first tubular member 522 for receiving an infusion fluid. Saline or other suitable infusion fluid 506 may be flushed through the infusion lumen 528 and into the lumen 538 of the infusion sheath 518. The infusion fluid 506 may displace blood from around the transducer 510. As the infusion fluid 506 flows past the ablation transducer 510, the infusion fluid 506 may provide convective cooling to the transducer 510. It is further contemplated that by displacing and/or cooling the blood surrounding the transducer 510, blood damage, fouling of the transducer 510, and/or overheating of the transducer 510 may be reduced or eliminated. In some instances, this may allow the modulation system 500 to be operated at a higher power level, thus providing a shorter treatment and/or more effective modulation of the target tissue. In some embodiments, the infusion sheath 518 may be structured to direct some or all of the infusion fluid 506 along the inside of the vessel wall 502. While blood flowing through the vessel lumen 504 removed some heat from the wall tissue, the addition of a "cooling" flush via infusion fluid 506 directed towards the vessel wall 502 may allow the application of more power for a shorter time period. It is contemplated that the infusion fluid 506 may be introduced into the modulation system 500 before, during, or after ablation. Flow of the infusion fluid 506 may begin before energy is supplied to the ablation transducer 510 and continue for the duration of the modulation procedure.

It is contemplated that the infusion sheath 518 may be formed from a material that is sonically translucent such that the ultrasound energy may pass through the infusion sheath 518. In some instances, the infusion sheath may be formed from a polymeric material having a low loss proper acoustic impedance. It is contemplated that the infusion sheath 518 may have a thickness such that significant attenuation of the ultrasound energy is avoided.

The infusion fluid 506 may be saline or any other suitable infusion fluid. It is contemplated that the infusion fluid 506 may be provided at a variety of different temperatures depending on the desired treatment. In some instances, the infusion fluid 506 may be provided at room temperature, below room temperature, above room temperature, or at normal body temperature as desired. In some instances, such as when an imaging transducer is provided (not explicitly shown), a small amount of an imaging contrast material may be added to the infusion fluid 506 to facilitate imaging of the vessel. Suitable examples of such imaging contrast material may include, but are not limited to fluorine, iodine, barium, or the like.

In some embodiments, the infusion sheath 518 may be configured to transition between an expanded state and a collapsed state. It is contemplated that the infusion sheath 518 may be self-expanding or may be expanded using an actuation mechanism Turning now to FIG. 6, a cross-section of a distal portion of another illustrative intravascular nerve modulation system 600 is depicted. The system 600 may include a hollow cylindrical ablation transducer 610, which may allow for cooling fluid 614 to pass through the lumen 609 of the transducer 610. The system 600 may further include an elongate catheter shaft 602 a support mandrel 612, and flexible mount members 606 and 616.

The catheter shaft 602 may include a first lumen 605, which may extend between a proximal end (not shown) and a distal end 603. The catheter shaft 602 is configured to be introduced within a body lumen (for example, body lumen 204 of FIG. 2). Although not shown, the proximal end of catheter shaft 602 may include a hub attached thereto for connecting other treatment devices or providing a port for facilitating other treatments. It is contemplated that the stiffness of the catheter shaft 602 may be modified to form the modulation system 600 for use in various vessel diameters and various locations within the vascular tree.

In the illustrated embodiment, the first lumen 605 may be configured to slidably receive a guidewire 620 therein. In some embodiments, a guide sheath similar to guide sheaths discussed above (not explicitly shown) may be used in addition to or in place of guidewire 620 to facilitate advancement of the system 600. In addition, the first lumen 605 may be employed for infusion of a fluid 614. Alternatively, the catheter shaft 602 may include separate lumen(s) (not shown) for infusion of fluid 614 or for other purposes such as introduction of a medical device, and so forth. The fluid 614 may facilitate cooling of the modulation system 600 and/or vessel wall during the ablation procedure. Further, the first lumen 605 may be configured in any way known in the art. For example, the first lumen 605 may extend along the entire length of the catheter shaft 602 such as in an over-the-wire catheter or may extend only along a distal portion of the catheter shaft 602 such as in a single operator exchange (SOE) catheter. These examples are not intended to be limiting, but rather examples of some possible configurations.

Further, the catheter shaft 602 may have a relatively long, thin, flexible tubular configuration. In some instances, the catheter shaft 602 may have a generally circular cross-section, however, other suitable configurations such as, but not limited to, rectangular, oval, irregular, or the like may also be contemplated. In addition, the catheter shaft 602 may have a cross-sectional configuration adapted to be received in a desired vessel, such as a renal artery. For instance, the catheter shaft 602 may be sized and configured to accommodate passage through the intravascular path, which leads from a percutaneous access site in, for example, the femoral, brachial, or radial artery, to a targeted treatment site, for example, within a renal artery.

Materials employed to manufacture the catheter shaft 602 may include any suitable biocompatible material. Examples may include metals, polymers, alloys, shape memory alloys, etc. Other suitable materials known in the art may also be employed.

Figure 6:
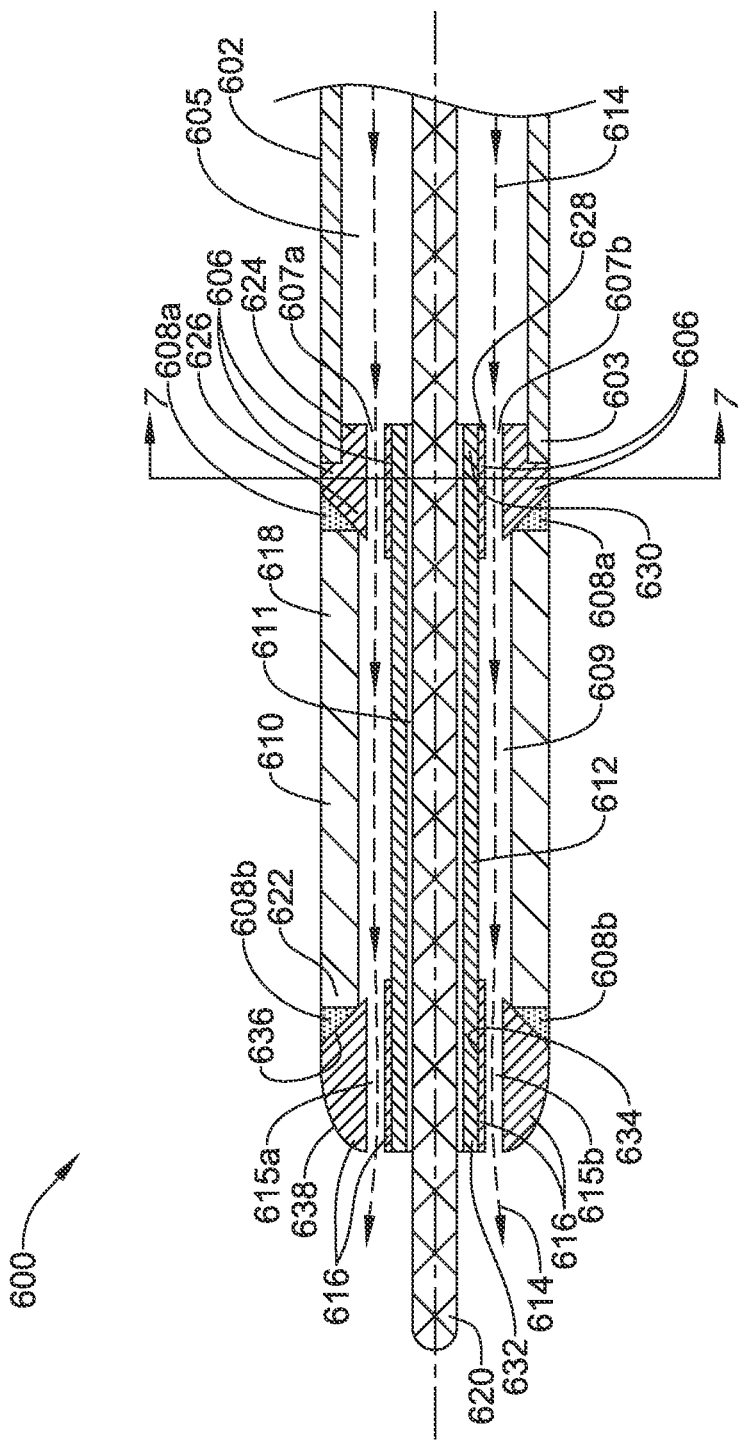
FIG. 6 illustrates a cross-sectional view of a portion of another illustrative intravascular nerve modulation system.

While FIG. 6 illustrates a single ablation transducer 610, it is contemplated that the modulation system 600 may include any number of ablation transducers desired, such as, but not limited to two, three, or more. The ablation transducer 610 is configured to deliver acoustic energy (i.e., ultrasound waves) to a target tissue. At the targeted tissue, the acoustic energy is converted to heat resulting in protein denaturation and coagulative necrosis of the tissue and/or nerves at the target region. In some instances, the frequency of the ultrasound energy used for the procedure may be set so that the ablated area of tissue starts after it passes through the vessel wall thereby minimizing potential heat damage of the vessel wall.

As shown, the ablation transducer 610 may have a hollow cylindrical shape that may define a lumen 609. The lumen 609 may remain in fluid communication with the first lumen 605 and the through holes 607. Those skilled in the art, however, will appreciate that any suitable shape such as, but not limited to, square, rectangular, polygonal, circular, oblong, or the like may also be contemplated.

While the ablation transducer 610 is described as an ultrasonic transducer, it is contemplated that other methods and devices for raising the temperature of the target tissue (e.g., nerve) may be used, such as, but not limited to: radiofrequency, microwave, other acoustic, optical, electrical current, direct contact heating, or other heating.

The ablation transducer 610 may be formed from any suitable material such as, but not limited to, lead zirconate titanate (PZT). It is contemplated that other ceramic or piezoelectric materials may also be used. In some instances, the ablation transducer 610 may include a layer of gold, or other conductive layer, disposed on the acoustically functional areas of the transducer 610 surface for connecting electrical leads to the ablation transducer 610. It is contemplated that the sides/edges of the transducer crystal may be free of conductive material so as not to "short circuit" the transducer 610. In some instances, one or more tie layers may be used to bond the gold to the PZT. For example, a layer of chrome may be disposed between the PZT and the gold to improve adhesion. In other instances, the transducer 610 may include a layer of chrome over the PZT followed by a layer of nickel, and finally a layer of gold. These are just examples. It is contemplated that the layers may be deposited on the PZT using sputter coating, although other deposition techniques may be used as desired.

Although not shown, the ablation transducer 610 may have a radiating surface, and a perimeter surface extending around the outer edge of the ablation transducer 610. The acoustic energy from the radiating surface of the ablation transducer 610 may be transmitted in a spatial pressure distribution related to the shape of the ablation transducer 610. For instance, the cylindrical shape of the ablation transducer 610 may provide a circumferential ablation pattern. In such an instance, the ablation transducer 610 may include a backing layer to direct the acoustic energy in a single direction. In other embodiments, the ablation transducer 610 may be structured to radiate acoustic energy from two radiating surfaces.

Further, the ablation transducer 610 can be operably coupled to the distal end 603 of the catheter shaft 602 through a first flexible mount member 606. As shown, the first flexible mount member 606 may have a generally trapezoidal shape, however, it should be noted that the flexible mount may take on any suitable shape such as rectangular, cylindrical, triangular, or the like. The first flexible mount member 606 may be affixed to the distal end 603 of the catheter shaft 602 at a proximal end 624, while being coupled to a proximal end 618 of the ablation transducer 610 at a distal end 626 thereof. In some instances, the first flexible mount 606 may include a proximal end 624 sized and shaped to be received within the lumen 605 of the catheter shaft 602, although this is not required. In some instances, the first flexible mount member 606 may be positioned along and secured to an outside surface of the catheter shaft 602. It is contemplated that the first flexible mount 606 may be secured to the catheter shaft 602 using any method desired, such as, but not limited to, adhesives, thermal bonding, heat shrinking, etc. The distal end 626 of the first flexible mount 606 may be secured to the proximal end 618 of the transducer 610 through a flexible adhesive 608a. In some instances, the flexible adhesive 608a may comprise silicone or other like materials.

Figure 7:
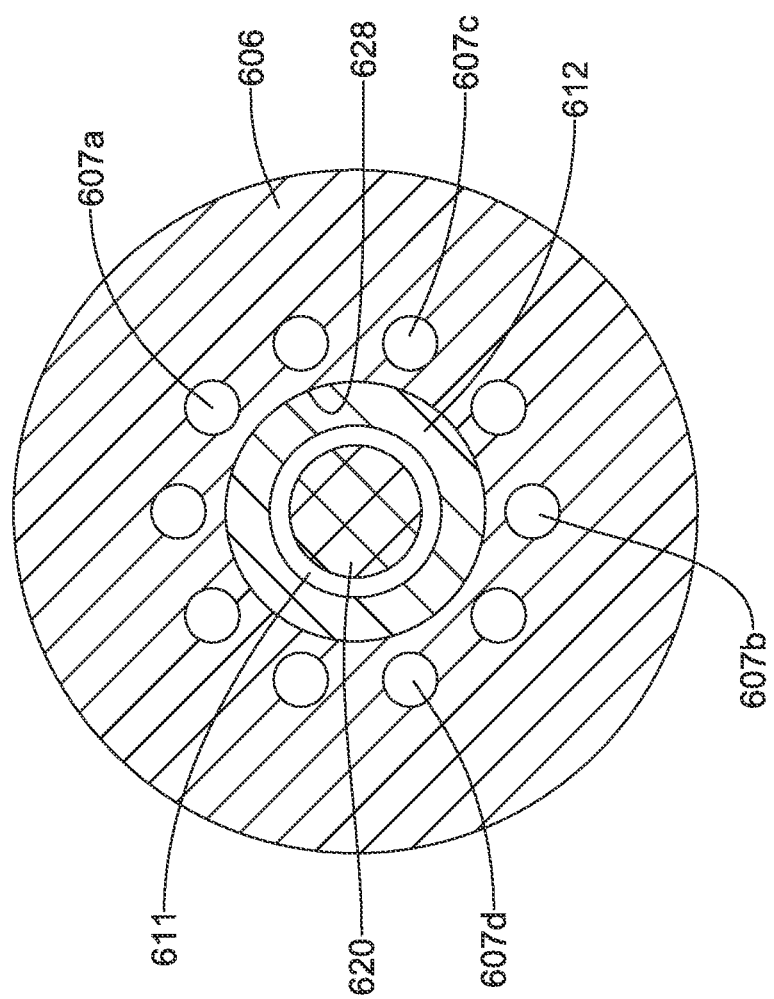
FIG. 7 illustrates a cross-sectional view of the illustrative nerve modulation system of FIG. 6.

Referring to FIGS. 6 and 7, the first flexible mount 606 may include a central lumen having an inner surface 628. The inner surface 628 may be fixedly secured to the proximal end 630 of the support mandrel 612 through any means desired. The first flexible mount 606 may further include one or more through holes 607a, 607b, 607c, 607d (collectively 607) extending from the proximal end 624 to the distal end 626 of the mount 606. For clarity, not all of the through holes 607 have been numbered in FIG. 7. The through holes 607 may be sized and shaped to allow an infusion fluid 614 to pass through the flexible mount 606. It is contemplated that the first flexible mount 606 may include any number of through holes desired, such as, but not limited to, one, two, three, four, or more. It is further contemplated that the through holes 607 may be arranged in any manner desired. For example, in some instances, the through holes 607 may be randomly scattered about the cross-section of the first flexible mount 606. In other instances, the through holes 607 may be arranged in a pattern. While FIG. 7 illustrates the through holes 607 as a single ring of holes, it is contemplated that there may be multiple rings (or other geometric configurations) across the cross-section of the first flexible mount 606. The through holes 607 may be in fluid communication with the first lumen 605 of the catheter shaft 602 and the lumen 609 of the transducer 610.

Further, the ablation transducer 610 can be operably coupled to the distal end 632 of the support mandrel 612 through a second flexible mount member 616. As shown, the second flexible mount member 616 may have a generally tapered proximal end 636 and a rounded atraumatic distal end 638, however, the second flexible mount may take on any suitable shape such as rectangular, cylindrical, triangular, or the like. The second flexible mount member 616 may be affixed to the distal end 622 of the ablation transducer 610 at a proximal end 636 thereof. The proximal end 636 of the second flexible mount 616 may be secured to the distal end 622 of the transducer 610 through a flexible adhesive 608b. In some instances, the flexible adhesive 608b may comprise silicone or other like materials.

The second flexible mount 616 may include a central lumen having an inner surface 634. The inner surface 634 may be fixedly secured to the distal end 632 of the support mandrel 612 through any means desired. The second flexible mount 616 may further include one or more through holes 615a, 615b (collectively 615) extending from the proximal end 636 to the distal end 638 of the mount 616. The through holes 615 may be sized and shaped to allow an infusion fluid 614 to pass through the flexible mount 616. It is contemplated that the second flexible mount 616 may include any number of through holes desired, such as, but not limited to, one, two, three, four, or more. number of through holes desired, such as, but not limited to, one, two, three, four, or more. It is further contemplated that the through holes 615 may be arranged in any manner desired. For example, in some instances, the through holes 615 may be randomly scattered about the cross-section of the second flexible mount 616. In other instances, the through holes 607 may be arranged in a pattern. The through holes 615 may be in fluid communication with the lumen 609 of the transducer 610 and may have a distal opening thus allowing the infusion fluid 614 to exit the system 600.

The support mandrel 612 may be configured to be disposed within the lumen 609 of the hollow cylindrical ablation transducer 610. As illustrated, the support mandrel may extend generally parallel with and along the length of the ablation transducer 610. As discussed above, the support mandrel 612 may be fixedly secured to inner lumens of the first and the second flexible mount members 606, 616. The flexible mounts 606, 616 may attached the transducer 610 to the support mandrel 612 to minimize interference with the transducer vibration. The support mandrel 612 may have a generally hollow cylindrical shape defining a lumen 611 extending from the proximal end 630 to the distal end 632 of the support mandrel 612. However, other suitable shapes of the support mandrel 612 including, for example, rectangular, irregular, or the like may also be contemplated. Further, the material employed to manufacture may include any suitable biocompatible material such as, but not limited to, metals, polymers, alloys, shape memory alloys or the like. The lumen 611 may be configured to receiving a guidewire 620 therethrough. In some embodiments, the lumen 611 may be in fluid communication with the lumen 605 of the catheter shaft 602 and thus some infusion fluid 614 may pass through lumen 611 and exit the system 600.

Saline or other suitable infusion fluid 614 may be flushed through the lumen 605 of the catheter shaft 602, through the through holes 607 of the first flexible mount 606, and into the lumen 609 of the transducer 610. The infusion fluid 614 may cool the transducer 610, reduce transducer damage, reduce surface fouling, reduce damage to the blood and other non-target tissue, and/or reduce overheating of the transducer 610 may be reduced or eliminated. The infusion fluid 614 may exit the system 600 via through holes 615 in the second flexible mount 616. It is contemplated that some infusion fluid 614 may also enter the lumen 611 of the support mandrel 613 from the lumen 605 of the catheter shaft 602 and exit the system via the distal end 632 of the support mandrel. In some instances, this may allow the modulation system 600 to be operated at a higher power level, thus providing a shorter treatment and/or more effective modulation of the target tissue. It is contemplated that the infusion fluid 614 may be introduced into the modulation system 600 before, during, or after ablation. Flow of the infusion fluid 614 may begin before energy is supplied to the ablation transducer 610 and continue for the duration of the modulation procedure.

Those skilled in the art will recognize that the present invention may be manifested in a variety of forms other than the specific embodiments described and contemplated herein. Accordingly, departure in form and detail may be made without departing from the scope and spirit of the present disclosure as described in the appended claims.

What is claimed is:

1. An intravascular nerve modulation system, comprising:
   an elongate shaft having a proximal end, a distal end, and an infusion lumen extending therebetween;
   an ablation transducer comprising an ultrasound transducer affixed to the elongate shaft adjacent the distal end thereof;
   an expandable basket having a proximal end and a distal end, the proximal end affixed to the elongate shaft proximal of a proximal end of the ablation transducer and the distal end is affixed to the elongate shaft distal of a distal end of the ablation transducer;
   an infusion sheath secured adjacent to the distal end of the elongate shaft in fluid communication with the infusion lumen, wherein the infusion sheath extends over the ablation transducer and is located within the expandable basket;

wherein the system is configured to transport infusion fluid through the infusion lumen and past the ablation transducer thereby providing convective cooling to the ablation transducer; and wherein the expandable basket is configured to actuate between a first collapsed configuration and a second expanded configuration.

2. The nerve modulation system of claim 1, further comprising one or more temperature sensors coupled to the expandable basket.

3. The nerve modulation system of claim 1, wherein the expandable basket comprises two or more generally longitudinally extending struts.

4. The nerve modulation system of claim 1, further comprising a pull wire affixed to one of the distal end or the proximal end of the expandable basket.

5. The nerve modulation system of claim 4, wherein actuation of the pull wire moves the expandable basket between the first collapsed position and the second expanded position.

6. The nerve modulation system of claim 1, wherein the expandable basket is configured to self-expand.

7. The intravascular nerve modulation system at claim 1, wherein the elongate shaft comprises a first tubular member and a second tubular member and wherein said infusion lumen is located between the first tubular member and the second tubular member.

8. The intravascular nerve modulation system of claim 1, wherein the ablation transducer is a hollow ablation transducer that comprises a transducer lumen in fluid communication with the infusion lumen.

9. The intravascular nerve modulation system of claim 8, further comprising a flexible mount, wherein the ablation transducer is affixed to the elongate shaft through the flexible mount, and wherein the flexible mount comprises one or more lumens establishing fluid communication between the infusion lumen and the transducer lumen to allow the infusion fluid to be transported through the transducer lumen.

10. An intravascular nerve modulation system, comprising:
    an elongate shaft having a proximal end region, a distal end region and an infusion lumen extending therebetween;
    an ablation transducer comprising an ultrasound transducer coupled to the distal end region of the shaft;
    an expandable basket coupled to the distal end region of the shaft, the expandable basket having a proximal end disposed proximal of the ablation transducer and a distal end disposed distal of the ablation transducer;
    an infusion sheath secured adjacent to the distal end of the elongate shaft in fluid communication with the infusion lumen, wherein the infusion sheath extends over the ablation transducer and is located within the expandable basket;
    wherein the system is configured to transport infusion fluid through the infusion lumen and past the ablation transducer thereby providing convective cooling to the ablation transducer;
    wherein the expandable basket is capable of shifting between a first configuration and an expanded configuration;
    and a sensor coupled to the expandable basket.

11. The intravascular nerve modulation system claim 10, wherein the sensor includes a temperature sensor.

12. The intravascular nerve modulation system of claim 11, wherein the sensor is designed to monitor the temperature of a vessel wall during an ablation procedure.

13. The intravascular nerve modulation system claim 10, wherein the sensor includes an impedance sensor.

14. The intravascular nerve modulation system of claim 10, wherein the sensor is designed to contact a vessel wall during an ablation procedure.

15. The intravascular nerve modulation system of claim 10, wherein the sensor is designed to monitor the progress of an ablation procedure.

16. The intravascular nerve modulation system of claim 10, wherein the expandable basket includes a plurality of struts and wherein the sensor is coupled to one of the struts.

17. The intravascular nerve modulation system of claim 10, wherein a plurality of sensors are coupled to the expandable basket.

18. An intravascular nerve modulation system, comprising:
    an elongate shaft having a proximal end region, a distal end region and an infusion lumen extending therebetween;
    an ultrasound transducer coupled to the distal end region of the shaft;
    an expandable basket coupled to the distal end region of the shaft, the expandable basket having a proximal end disposed proximal of the ultrasound transducer and a distal end disposed distal of the ultrasound transducer;
    an infusion sheath secured adjacent to the distal end of the elongate shaft in fluid communication with the infusion lumen, wherein the infusion sheath extends over the ablation transducer and is located within the expandable basket;
    wherein the system is configured to transport infusion fluid through the infusion lumen and past the ablation transducer thereby providing convective cooling to the ablation transducer;
    wherein the expandable basket is capable of shifting between a first configuration and an expanded configuration;
    a sensor coupled to the expandable basket;
    wherein the sensor is capable of contacting a vessel wall when the basket is in the expanded configuration; and
    wherein the sensor is designed to monitor the progress of ablation by the ultrasound transducer during an ablation procedure.

19. The intravascular nerve modulation system claim 18, wherein the sensor includes a temperature sensor, an impedance sensor, or both.

* * * * *